US009789224B2

(12) United States Patent
Christman et al.

(10) Patent No.: US 9,789,224 B2
(45) Date of Patent: Oct. 17, 2017

(54) COMPOSITIONS AND METHODS FOR CARDIAC THERAPY

(75) Inventors: Karen Christman, San Diego, CA (US); Jennifer Singelyn, Riverdale, NJ (US); Jessica Dequach, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/217,218

(22) Filed: Aug. 24, 2011

(65) Prior Publication Data
US 2012/0156250 A1 Jun. 21, 2012

Related U.S. Application Data

(60) Provisional application No. 61/376,654, filed on Aug. 24, 2010.

(51) Int. Cl.
| A61F 13/00 | (2006.01) |
| A61L 27/36 | (2006.01) |
| A61K 35/34 | (2015.01) |
| A61K 38/48 | (2006.01) |
| A61L 27/20 | (2006.01) |
| A61L 27/56 | (2006.01) |
| A61L 27/50 | (2006.01) |

(52) U.S. Cl.
CPC .......... *A61L 27/3633* (2013.01); *A61K 35/34* (2013.01); *A61K 38/488* (2013.01); *A61L 27/20* (2013.01); *A61L 27/3625* (2013.01); *A61L 27/3683* (2013.01); *A61L 27/3687* (2013.01); *A61L 27/50* (2013.01); *A61L 27/56* (2013.01); *A61L 2400/06* (2013.01); *A61L 2430/20* (2013.01)

(58) Field of Classification Search
CPC ... A61K 9/0019; A61K 9/0021; A61K 9/0024
USPC .................................. 424/489–495
See application file for complete search history.

(56) References Cited

U.S. PATENT DOCUMENTS

| 4,902,508 A | 2/1990 | Badylak et al. |
| 4,956,178 A | 9/1990 | Badylak et al. |
| 4,970,298 A | 11/1990 | Silver et al. |
| 5,171,262 A | 12/1992 | MacGregor |
| 5,275,826 A | 1/1994 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,631,019 A | 5/1997 | Marx |
| 5,645,860 A | 7/1997 | Knapp, Jr. et al. |
| 5,665,391 A | 9/1997 | Lea et al. |
| 5,711,969 A | 1/1998 | Patel et al. |
| 5,741,701 A | 4/1998 | Swiderek et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 5,885,619 A | 3/1999 | Patel et al. |
| 5,955,110 A | 9/1999 | Patel et al. |
| 5,968,096 A | 10/1999 | Whitson et al. |
| 6,099,567 A | 8/2000 | Badylak et al. |
| 6,187,039 B1 | 2/2001 | Hiles et al. |
| 6,264,992 B1 | 7/2001 | Voytik-Harbin et al. |
| 6,379,710 B1 | 4/2002 | Badylak |
| 6,444,229 B2 | 9/2002 | Voytik-Harbin et al. |
| 6,485,723 B1 | 11/2002 | Badylak et al. |
| 6,551,618 B2 | 4/2003 | Baird et al. |
| 6,554,857 B1 | 4/2003 | Zilla et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak et al. |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |

(Continued)

FOREIGN PATENT DOCUMENTS

| WO | WO 03/094697 A1 | 11/2003 |
| WO | WO 2003/094697 A1 | 11/2003 |

(Continued)

OTHER PUBLICATIONS

Slngleyn, et al, Naturally derived myocardial matrix as an injectable scaffold for cardiac tissue engineering, Biomaterials, vol. 30, Issue 29, Oct. 2009, pp. 5409-5416.*
Badylak, et al. Extracellular matrix for myocardial repair. The Heart Surgery Forum. 2003; 6(2):E20-6.
European search report and search opinion dated Jun. 12, 2012 for EP Application No. 09818438.5.
International search report and written opinion dated Apr. 30, 2012 for PCT/US2011/049026.
Jawad, et al. Myocardial tissue engineering. Br Med Bull. 2008;87:31-47.
Qing, et al. Optimal method for rat skeletal muscle decellularization. Zhongguo Xiu Fu Chong Jian Wai Ke Za Zhi. Jul. 2009;23(7):836-9. (English abstract only).
Freytes, et al. Preparation and rheological characterization of a gel form of the porcine urinary bladder matrix. Biomaterials. Apr. 2008;29(11):1630-7. Epub Jan. 16, 2008.

(Continued)

*Primary Examiner* — Micah-Paul Young
(74) *Attorney, Agent, or Firm* — Wilson Sonsini Goodrich & Rosati

(57) ABSTRACT

Provided herein are methods and compositions for cardiac therapy. Such compositions include extracellular-matrix (ECM)-based products that can be used to support tissue repair. The compositions can be used for various purposes. In some cases, they can be introduced into a subject in order to preserve and/or repair damaged heart tissue.

18 Claims, 4 Drawing Sheets

(56) References Cited

U.S. PATENT DOCUMENTS

| | | | |
|---|---|---|---|
| 6,932,804 B2 | 8/2005 | Lee | |
| 7,235,295 B2 | 6/2007 | Laurencin et al. | |
| 7,252,819 B2 | 8/2007 | Lee | |
| 7,875,017 B2 | 1/2011 | Sabbah et al. | |
| 8,110,561 B2 | 2/2012 | Cohen et al. | |
| 8,168,612 B2 | 5/2012 | Cohen et al. | |
| 8,361,503 B2 | 1/2013 | Badylak et al. | |
| 8,691,276 B2 | 4/2014 | Badylak et al. | |
| 2001/0014475 A1 | 8/2001 | Frondoza et al. | |
| 2002/0085994 A1 | 7/2002 | Ceres et al. | |
| 2002/0090725 A1 | 7/2002 | Simpson et al. | |
| 2003/0012822 A1 | 1/2003 | Voytik-Harbin et al. | |
| 2003/0100944 A1 | 5/2003 | Laksin et al. | |
| 2004/0002740 A1 | 1/2004 | Lee | |
| 2004/0009600 A1 | 1/2004 | Bowlin et al. | |
| 2005/0003010 A1 | 1/2005 | Cohen et al. | |
| 2005/0013870 A1* | 1/2005 | Freyman | A61L 27/3633 424/520 |
| 2005/0013872 A1 | 1/2005 | Freyman | |
| 2005/0181016 A1 | 8/2005 | Freyman et al. | |
| 2006/0134079 A1 | 6/2006 | Sih et al. | |
| 2006/0147433 A1 | 7/2006 | Hiles | |
| 2006/0149309 A1 | 7/2006 | Paul et al. | |
| 2006/0153815 A1* | 7/2006 | Seyda et al. | 424/93.7 |
| 2006/0253192 A1* | 11/2006 | Atala | A61F 2/2415 623/2.13 |
| 2007/0014755 A1 | 1/2007 | Beckman et al. | |
| 2007/0014773 A1 | 1/2007 | Matheny et al. | |
| 2007/0014870 A1 | 1/2007 | Matheny | |
| 2007/0014871 A1 | 1/2007 | Matheny et al. | |
| 2007/0014872 A1 | 1/2007 | Matheny et al. | |
| 2007/0014873 A1 | 1/2007 | Matheny | |
| 2007/0014874 A1 | 1/2007 | Matheny | |
| 2007/0248638 A1* | 10/2007 | Van Dyke et al. | A61K 35/22 424/422 |
| 2008/0065046 A1 | 3/2008 | Sabbah et al. | |
| 2008/0065048 A1 | 3/2008 | Sabbah et al. | |
| 2008/0260831 A1* | 10/2008 | Badylak | A61K 35/12 424/484 |
| 2009/0012413 A1 | 1/2009 | Sabbah et al. | |
| 2010/0190741 A1 | 7/2010 | Cohen et al. | |
| 2011/0189140 A1 | 8/2011 | Christman et al. | |
| 2013/0101563 A1 | 4/2013 | Matheny et al. | |
| 2013/0116198 A1 | 5/2013 | Matheny et al. | |
| 2013/0122108 A1 | 5/2013 | Matheny et al. | |
| 2013/0123176 A1 | 5/2013 | Matheny et al. | |
| 2013/0123348 A1 | 5/2013 | Matheny et al. | |
| 2013/0129831 A1 | 5/2013 | Matheny et al. | |
| 2013/0129833 A1 | 5/2013 | Matheny et al. | |
| 2013/0129834 A1 | 5/2013 | Matheny et al. | |
| 2013/0156862 A1 | 6/2013 | Badylak et al. | |
| 2013/0251687 A1 | 9/2013 | Christman et al. | |
| 2013/0266546 A1 | 10/2013 | Matheny et al. | |
| 2013/0266547 A1 | 10/2013 | Matheny et al. | |
| 2013/0266548 A1 | 10/2013 | Matheny et al. | |

FOREIGN PATENT DOCUMENTS

| | | | |
|---|---|---|---|
| WO | WO 2004/050013 A1 | 6/2004 | |
| WO | WO 2004/098669 A1 | 11/2004 | |
| WO | WO 2006/021950 A1 | 3/2006 | |
| WO | WO 2006/095342 A2 | 9/2006 | |
| WO | WO 2006095342 A2 * | 9/2006 | |
| WO | WO 2006/095342 A3 | 3/2007 | |
| WO | WO 2008/109407 A2 | 9/2008 | |
| WO | WO 2009/089110 A2 | 7/2009 | |
| WO | WO 2009/089110 A3 | 3/2010 | |
| WO | WO 2010/039823 A2 | 4/2010 | |
| WO | WO 2010039823 A2 * | 4/2010 | A61K 35/34 |
| WO | WO 2010/039823 A3 | 7/2010 | |

OTHER PUBLICATIONS

International search report and written opinion dated Apr. 19, 2010 for PCT/US2009/059015.

Leor, et al. Cells, scaffolds, and molecules for myocardial tissue engineering. Pharmacol Ther. Feb. 2005;105(2):151-63. Epub Dec. 8, 2004.

Ott, et al. Perfusion-decellularized matrix: using nature's platform to engineer a bioartificial heart. Nat Med. Feb. 2008;14(2):213-21. Epub Jan. 13, 2008.

Stella, et al. On the biomechanical function of scaffolds for engineering load-bearing soft tissues.Acta Biomater. Jul. 2010;6(7):2365-81. Epub Jan. 7, 2010.

Badylak, et al. Esophageal reconstruction with ECM and muscle tissue in a dog model. J Surg Res. Sep. 2005;128(1):87-97.

Badylak, et al. Naturally occurring extracellular matrix as a scaffold for musculoskeletal repair. Clin Orthop Relat Res. Oct. 1999;(367 Suppl):S333-43.

Badylak, et al. Resorbable bioscaffold for esophageal repair in a dog model. J Pediatr Surg. Jul. 2000;35(7):1097-103.

Badylak, et al. The use of extracellular matrix as an inductive scaffold for the partial replacement of functional myocardium. Cell Transplant. 2006;15 Suppl 1:S29-40.

Badylak, et al. The use of xenogeneic small intestinal submucosa as a biomaterial for Achilles tendon repair in a dog model. J Biomed Mater Res. Aug. 1995;29(8):977-85.

Badylak. The extracellular matrix as a scaffold for tissue reconstruction. Semin Cell Dev Biol. Oct. 2002;13(5):377-83.

Badylak. Xenogeneic extracellular matrix as a scaffold for tissue reconstruction. Transpl Immunol. Apr. 2004;12(3-4):367-77.

Bernacca, et al. Polyurethane heart valve durability: effects of leaflet thickness and material. Int J Artif Organs. Jun. 1997;20(6):327-31.

Billiar, et al. Biaxial mechanical properties of the natural and glutaraldehyde treated aortic valve cusp—Part I: Experimental results. J Biomech Eng. Feb. 2000;122(1):23-30.

Brightman, et al. Time-lapse confocal reflection microscopy of collagen fibrillogenesis and extracellular matrix assembly in vitro. Biopolymers. Sep. 2000;54(3):222-34.

Chaudhuri, et al. Detection and gradation of oriented texture. Pattern Recogn Lett. 1993;14(2):147-53.

Courtney, et al. Analysis and design of novel electrospun PEUU scaffolds for soft tissue engineering. The 8th Annual Meeting of the Tissue Engineering Society International, Oct. 22-25 2005, Shanghai, P.R. China. Published on CD, Final Program and Abstract Book TESI 2005, Abstract# 193.

Courtney, et al. Analysis and design of novel electrospun PEUU scaffolds for soft tissue engineering. ASME 2005 Summer Bioengineering Conference, Vail, CO, Jun. 22-26, 2005. Published on CD, Proceedings of the 2005 Summer Bioengineering Conference Vail Cascade Resort and Spa, Vail, CO; Abstract# b0241329.

Courtney, et al. Analysis and design of novel electrospun PEUU scaffolds for soft tissue engineering. 2005 Annual Fall Mtg, Nov. 28-Dec. 1, 2005, Boston, MA. Abstract L 13.1.

Courtney, et al. Design and analysis of tissue engineering scaffolds that mimic soft tissue mechanical anisotropy. Biomaterials. Jul. 2006;27(19):3631-8. Epub Mar. 20, 2006.

Courtney, et al. Incorporation of fiber tortuosity effects in a constitutive model for scaffolds. ASME 2006 Summer Bioengineering Conference, Jun. 21-25, 2006, Amelia Island, Florida. Published on CD, Proceedings of the 2006 Summer Bioengineering Conference, Abstract# BIO2005-157686.

Courtney, et al. Meso- and micromechanics of elastomeric electrospun PEUU scaffolds for cardiovascular tissue engineering. Regenerate World Congress on Tissue Engineering and Regenerative Medicine, Apr. 25-27, 2006, Pittsburgh, PA. Published on CD, Conference Proceedings Regenerate World Congress on Tissue Engineering and Regenerative Medicine, Abstract # 572.

Courtney, et al. Micromechanics of electrospun poly ester urethane urea scaffolds for soft tissue engineering. Fifth World Congress of Biomechanics, Jul. 29-Aug. 4, 2006, Munich, Germany. Published in Journal of Biomechanics 2006 39(Supp 1 ): S262.

Courtney, et al. Micromechanics of electrospun polyester urethane urea scaffolds. Society for Biomaterials 2006 Annual Meeting, Apr. 26-29, 2006, Pittsburgh, PA. Published on CD, Transactions of the

(56) References Cited

OTHER PUBLICATIONS

31st Annual Meeting of the Society for Biomaterials, vol. XXIX, Abstract# 163.
Courtney, et al. Structural and mechanical characterization of poly(ester urethane) elastomeric scaffolds for cardiovascular soft tissue engineering. Society for Biomaterials 30th Annual Meeting, Memphis, TN, Apr. 27-30, 2005. Published on CD, Transactions of the 30th Annual Meeting.
De La Fuente, et al. Evaluation of porcine-derived small intestine submucosa as a biodegradable graft for gastrointestinal healing. J Gastrointest Surg. 96-1 01 (7) 2003.
Dedecker, et al. Small intestinal submucosa (SIS): prospects in urogenital surgery. Prog Urol. Jun. 2005;15(3):405-10. (English-language Abstract included).
Deglau, et al. Surface modification of vascular tissue for targeted delivery of endothelial cells and microspheres. Abstract for Biomedical Engineering Society 2000 Annual Fall Meeting, Oct. 12-14, 2000. Ann Biomed Eng. 2000;28(Supplement):S-23.
Dejardin, et al. Tissue-engineered rotator cuff tendon using porcine small intestine submucosa. Histologic and mechanical evaluation in dogs. AJSM. 175-84 (29) 2001.
Duruisseau, et al. Endoscopic rehabilitation of vocal cord paralysis with a silicone elastomer suspension implant. Otolaryngol Head Neck Surg. Sep. 2004;131(3):241-7.
European search report and search opinion dated Sep. 25, 2014 for EP Application No. 11820625.9.
Freytes, et al. Biaxial strength of multilaminated extracellular matrix scaffolds. Biomaterials, 2004. 25(12): 2353-61.
Freytes, et al. Porcine Urinary Bladder Matrix Derived Gel for Tissue Engineering Applications. Regenerate World Congress and Society for Biomaterials: 2006. Pittsburgh, PA. (Poster and Abstract).
Frisk, et al. A concept for miniaturized 3-D cell culture using an extracellular matrix gel. Electrophoresis. Dec. 2005;26(24):4751-8.
Gelman, et al. Collagen fibril formation. Evidence for a multistep process. J Bioi Chem. Jan. 10, 1979;254(1):180-6.
Gilbert, et al. Development of a Hybrid ECM/Porous Metal Scaffold for Connective Tissue Ingrowth. Regenerate World Congress Meeting: Apr. 2006. Pittsburgh, PA. (Poster and Abstract).
Grashow, et al. Biaixal stress-stretch behavior of the mitral valve anterior leaflet at physiologic strain rates. Ann Biomed Eng. Feb. 2006;34(2):315-25. Epub Feb. 1, 2006.
Guan, et al. Biodegradable poly(ether ester urethane)urea elastomers based on poly(ether ester) triblock copolymers and putrescine: synthesis, characterization and cytocompatibility. Biomaterials. Jan. 2004;25(1):85-96.
Guan, et al. Preparation and characterization of highly porous, biodegradable polyurethane scaffolds for soft tissue applications. Biomaterials. Jun. 2005;26(18):3961-71.
Guan, et al. Synthesis, characterization and cytocompatibility of polyurethaneurea elastomers with designed elastase sensitivity. Biomacromolecules. Sep.-Oct. 2005;6(5):2833-42.
Guan, et al. Synthesis, characterization, and cytocompatibility of elastomeric, biodegradable poly(ester-urethane)ureas based on poly(caprolactone) and putrescine. J Biomed Mater Res. Sep. 5, 2002;61(3):493-503.
Hacking, et al. Fibrous tissue ingrowth and attachment to porous tantalum. J Biomed Mater Res, 631-8 (52) 2000.
Higuera, et al. Tendon reattachment to a metallic implant using an allogenic bone plate augmented with rhOP-1 vs. autogenous cancellous bone and marrow in a canine model. J Orthop Res. Sep. 2005;23(5):1 091-9. Epub Apr. 7, 2005.
Karlon, et al. Automated measurement of myofiber disarray in transgenic mice with ventricular expression of ras. Anat Rec. Dec. 1998;252(4):612-25.
Lee, et al. Nanofiber alignment and direction of mechanical strain affect the ECM production of human ACL fibroblast. Biomaterials. Apr. 2005;26(11):1261-70.

Lehman. Injectable and bulk-forming agents for enhancing the lower esophageal sphincter. Am J Med. Aug. 18, 2003;115 Suppl 3A:188S-91 S.
Lightner, et al. Injectable agents: present and future. Curr Urol Rep. Oct. 2002;3(5):408-13.
Matsuda, et al. Mechanoactive scaffold design of small-diameter artificial graft made of electrospun segmented polyurethane fabrics. J Biomed Mater Res A. Apr. 1, 2005;73(1):125-31.
Middleton, et al. Synthetic Biodegradable Polymers as Medical Devices. Medical Plastics and Biomaterials Magazine. Medical Plastics and Biomaterials Magazine. Mar. 1998, p. 30. Available at: http://devicel in k.co m/m pb/ arch ive/98/03/002. htm I.
Nedovic, et al. Cell immobilization by electrostatic droplet generation. Landbauforsch Volk 2002, (241):11-17.
Office action dated Jan. 19, 2012 for U.S. Appl. No. 12/040,140.
Office action dated Jul. 22, 2013 for U.S. Appl. No. 13/684,830.
Radisic, et al. Medium perfusion enables engineering of compact and contractile cardiac tissue. Am J Physiol Heart Circ Physiol. Feb. 2004;286(2):H507-16. Epub Oct. 9, 2003.
Ray, et al. Isolation of vascular smooth muscle cells from a single murine aorta. Methods Cell Sci. 2001;23(4):185-8.
Reddy, et al. A simplified method for the analysis of hydroxyproline in biological tissues. Clin Biochem. Jun. 1996;29(3):225-9.
Riboldi, et al. Electrospun degradable polyesterurethane membranes: potential scaffolds for skeletal muscle tissue engineering. Biomaterials. Aug. 2005;26(22):4606-15. Epub Jan. 7, 2005.
Rimsay, et al. Biochemical Analysis of Hyaline Gelation: An Essential Step in the Assembly of the Sea Urchin Extraembryonic Matrix, the Hyaline Layer. Archives of Biochemistry and Biophysics. 2003; (414): 279-286.
Ringel, et al. The application of tissue engineering procedures to repair the larynx. J Speech Lang Hear Res. Feb. 2006;49(1):194-208.
Robinson, et al. Extracellular matrix scaffold for cardiac repair. Circulation. Aug. 30, 2005;112(9 Suppl):I135-43.
Robinson. Roles for Ca2+, Mg2+ and NaCI in modulating the self-association reaction of hyalin, a major protein component of the sea-urchin extraembryonic hyaline layer. Biochem J. Nov. 15, 1988;256(1):225-8.
Sacks. Biaxial mechanical evaluation of planar biological materials. J Elasticity 2000; 61(1-3):199-246.
Santucci, et al. Resorbable extracellular matrix grafts in urologic reconstruction. lnt Braz J Urol. May-Jun. 2005;31 (3):192-203. Review. Erratum in: lnt Braz J Urol. Jul.-Aug. 2005;31 (4):414.
Sarikaya, et al. Antimicrobial activity associated with extracellular matrices. Tissue Eng. Feb. 2002;8(1):63-71.
Stankus, et al. Fabrication of biodegradable elastomeric scaffolds with sub-micron morphologies. J Biomed Mater Res A. Sep. 15, 2004;70(4):603-14.
Stankus, et al. Fabrication of cell microintegrated blood vessel constructs through electrohydrodynamic atomization. Biomaterials. Jun. 2007;28(17):2738-46. Epub Feb. 20, 2007.
Stankus, et al. Microintegrating smooth muscle cells into a biodegradable, elastomeric fiber matrix. Biomaterials. Feb. 2006;27(5):735-44. Epub Aug. 10, 2005.
Suwiwat, et al. Expression of extracellular matrix components versican, chondroitin sulfate, tenascin, and hyaluronan, and their association with disease outcome in node-negative breast cancer. Clin Cancer Res. Apr. 1, 2004;10(7):2491-8.
Temple, et al. Electrostatic transportation of living cells through air. Abstracts of Papers, 223 ACS National Meeting, Orlando, FL, Apr. 7-11, 2002.
Veazey, et al. Mammalian cell delivery via aerosol deposition. J Biomed Mater Res B Appl Biomater. Feb. 15, 2005;72(2):334-8.
Venere, et al. New materials hold promise for human healing applications. Purdue News, Mar. 22, 2001.
Williams, et al. Optimal in vitro conditions and preliminary kinetic results. J Bioi Chem. Sep. 25, 1978;253(18):6578-85.
Wood, et al. Use of a particulate extracellular matrix bioscaffold for treatment of acquired urinary incontinence in dogs. J Am Vet Med Assoc. Apr. 1, 2005;226(7):1 095-7.

(56) References Cited

OTHER PUBLICATIONS

Wright Medical Technology. Comparative analysis: GRAFT JACKET™ Periosteum Replacement Scaffold & SIS™ Porcine Small Intestine Submucosa. Copyright in 2002.
Xu, et al. Aligned biodegradable nanofibrous structure: a potential scaffold for blood vessel engineering. Biomaterials. Feb. 2004;25(5):877-86.
Xu, et al. Injectable tissue-engineered cartilage with different chondrocyte sources. Plast Reconstr Surg. Apr. 15, 2004;113(5):1361-71.
Zantop, et al. Extracellular matrix scaffolds are repopulated, in part, by bone marrow-derived cells in a mouse model of achilles tendon reconstruction. J Orthop Res. Jun. 2006;24(6):1299-309.
Zhang, et al. Artificial matrix helps neonatal cardiomyocytes restore injured myocardium in rats. Artif Organs. Feb. 2006;30(2):86-93.
Danielsen, C.C. Mechanical properties of reconstituted collagen fibrils. Influence of a glycosaminoglycan: dermatan sulfate. Connective tissue research 1982;9(4):219-25.
Lungu, A. The influence of glycosaminoglycan type on the collagen-glycosaminoglycan porous scaffolds. Digest Journal of Nanomaterials and Bioustructures 2011;6(4):1867-1875.
Madden, et al. Proangiogenic scaffolds as functional templates for cardiac tissue engineering. Proc Natl Acad Sci U S A. Aug. 24, 2010;107(34):15211-6. doi: 10.1073/pnas.1006442107. Epub Aug. 9, 2010.
Obrink, B. The influence of glycosaminoglycans on the formation of fibers from monomeric tropocollagen in vitro. European journal of biochemistry / FEBS 1973;34(1):129-37.
Office action dated Jan. 10, 2013 for U.S. Appl. No. 13/075,774.
Office action dated May 18, 2012 for U.S. Appl. No. 13/075,774.
Seif-Naraghi, et al. Design and characterization of an injectable pericardial matrix gel: a potentially autologous scaffold for cardiac tissue engineering. Tissue Eng Part A. Jun. 2010;16(6):2017-27. doi: 10.1089/ten.TEA.2009.0768.
Singelyn, et al. Naturally derived myocardial matrix as an injectable scaffold for cardiac tissue engineering. Biomaterials. Oct. 2009;30(29):5409-16. doi: 10.1016/j.biomaterials.2009.06.045. Epub Jul. 15, 2009.
Wainwright, et al. Preparation of cardiac extracellular matrix from an intact porcine heart. Tissue engineering. Part C, Methods 2010;16(3):525-32.
Badylak, et al. Extracellular matrix as a biological scaffold material: structure and function. Acta Biomaterials 5 (2009): 1-13.
Bopassa, et al. Abstract 27: Paclitaxel Protects Heart from Cold Ischemia Through Inhibition of Mitochondrial Permeability Transition Pore (MPTP) Opening and Reduction of Myocardial Necrosis. Circulation. 2006; 114. p. 1.
DrugBank: Paclitaxel (DB01229). Downloaded on Feb. 17, 2015 from www.drugbank.ca/drugs/DB01229. p. 1-17.
Office action dated Feb. 25, 2015 for U.S. Appl. No. 13/891,562.
Office action dated Oct. 13, 2015 for U.S. Appl. No. 13/891,562.
Rosso, et al. From Cell-ECM Interactions to Tissue Engineering. Journal of Cellular Physiology, 199:174-180 (2004).
Wolf, et al. A hydrogel derived from decellularized dermal extracellular matrix. Biomaterials. Oct. 2012;33(29):7028-38. doi: 10.1016/j.biomaterials.2012.06.051. Epub Jul. 11, 2012.
Kornowski, et al. Electromagnetic guidance for catheter-based transendocardial injection: a platform for intramyocardial angiogenesis therapy. Results in normal and ischemic porcine models. J Am Coll Cardiol. Mar. 15, 2000;35(4):1031-9.
Office action dated Jul. 11, 2016 for U.S. Appl. No. 13/891,562.
Sheng, et al. Current Stem Cell Delivery Methods for Myocardial Repair. BioMed Research International. vol. 2013 (2013), Article ID 547902, 15 pages. http://dx.doi.org/10.1155/2013/547902.
Sherman, et al. Catheter-based delivery of cells to the heart. Nat Clin Pract Cardiovasc Med. Mar. 2006;3 Suppl 1:S57-64.
Office action dated Feb. 24, 2016 for U.S. Appl. No. 13/891,562.

* cited by examiner

COMPOSITIONS AND METHODS FOR CARDIAC THERAPY

CROSS-REFERENCE

This application claims the benefit of U.S. Provisional Application No. 61/376,654, filed Aug. 24, 2010, which application is incorporated herein by reference in its entirety.

BACKGROUND OF THE INVENTION

Cardiovascular disease is the leading cause of death in the United States. The most common cause of cardiovascular disease is myocardial infarction (MI), which occurs when a coronary artery is occluded. Approximately 37% of MI patients will die from heart failure within one year, and of those who do survive, two-thirds do not make a complete recovery. MI results in the death of cardiomyocytes and extracellular matrix (ECM) degradation, followed by scar deposition. Eventually heart failure is onset, and the heart dilates, leading to decreased pumping efficiency. As there are very few cardiac progenitors in the heart, heart tissue does not regenerate. Current treatments for heart failure rely heavily on invasive surgical procedures and do little to repair damaged heart tissue.

Current efforts to prevent heart failure after myocardial infarction (MI) have focused on cellular transplantation to replace necrotic cardiomyocytes, prevent negative left ventricular (LV) remodeling, and regenerate or repair heart tissue. However, without the proper matrix, cardiomyocyte growth in vitro and survival in vivo have been poor. There is a need for a gel or solution form of heart extracellular matrix for cardiac repair, arrhythmia treatment, and cell culture.

SUMMARY OF THE INVENTION

In an aspect, a composition comprises a material with a pore size of about 30 to 40 microns, wherein the material is injectable through a catheter with an inner diameter of 25 G or smaller.

In some instances, the material comprises: decellularized extracellular matrix derived from cardiac tissue; and water. In some instances, the material further comprises a saline solution.

In some instances, the composition is in a gel form within 30 minutes after delivery to in vivo tissue. In some instances, the material further comprises at least one digestive enzyme. In some instances, the at least one digestive enzyme cleaves the matrix such that the composition gels at greater than 20, 25, 30, or 35° C. In some instances, the at least one digestive enzyme cleaves the matrix such that the composition gels in less than 30, 20, 10, 5, or 1 minutes. In some instances, the at least one digestive enzyme is pepsin.

The material can be derived from ventricular tissue, further the material can be derived from left ventricular tissue. In some instances, the material further comprises a growth factor, a synthetic polymer, a naturally derived polymer, or a combination thereof. In some instances, the material further comprises cellulose. In some instances, the material comprises fibrin glue.

In some instances, the material comprises factors that promote survival of endogenous cardiomyocytes and cardiac cells, factors that prevent apoptosis of endogenous cardiomyocytes and cardiac cells, factors that promote neovascularization, factors that promote cell infiltration, factors that alter the immune response, factors that alter the inflammatory response, or a combination thereof.

In another aspect, a composition comprises: decellularized extracellular matrix derived from cardiac tissue; a biocompatible metal; and water. In some instances, the metal is metal fibers. In some instances, the metal is metal particles.

In yet another aspect, a composition is disclosed that comprises: decellularized extracellular matrix derived from cardiac tissue; alginate; and water.

In an aspect, a composition comprises: decellularized extracellular matrix derived from cardiac tissue, wherein the matrix comprises material of a molecular weight of less than 300 kDa, less than 200 kDa, less than 100 kDa, less than 50 kDa, or less than 20 kDa. In an aspect, a composition comprises: decellularized extracellular matrix derived from cardiac tissue, wherein the matrix comprises nonaqueous material of a molecular weight of less than 300 kDa, less than 200 kDa, less than 100 kDa, less than 50 kDa, or less than 20 kDa. In an aspect, a composition comprises: decellularized extracellular matrix derived from cardiac tissue, wherein the matrix comprises material of a molecular weight in a range with an upper limit of 300 kDa, 200 kDa, 100 kDa, 50 kDa, or 20 kDa and a lower limit of 0.5 kDa, 1 kDa, 2 kDa, 5 kDa, 10 kDa or 20 kDa.

In another aspect, a composition comprises: a lyophilized decellularized extracellular matrix derived from cardiac tissue; and glycosaminoglycan, wherein the composition comprises glycosaminoglycan in the amount of at least 5, 10, or 15 µg per mg of the lyophilized matrix. In some instances, the composition comprises glycosaminoglycan in the amount of between about 15 to 25 µg per mg of the lyophilized matrix.

In yet another aspect, a tissue culture device is disclosed that comprises: a composition comprising decellularized extracellular matrix derived from cardiac tissue; and a substrate. The substrate can be a tissue culture plate. The matrix can be in the shape of a mold. In some instances, the matrix is molded to the shape of the substrate. Exemplary shapes may be those of biomedical products, such as stents or catheters. Other shapes may include those configured to shape to the heart in vivo. The substrate can be cellulose. In some instances, the cellulose is in a shape for implantation into a subject. In some instances, the device further comprises a tissue culture medium. In some instances, the shape is a tissue culture shape such as, without limitation, a dish, a vial, a petri dish, a plate, a well, and a multiwall plate.

In an aspect, a method of manufacturing a composition is described herein, the method comprising: decellularizing cardiac tissue; lyophilizing the decelled cardiac tissue; digesting the lyophilized tissue; lyophilizing the digested tissue; storing the digested tissue for up to 6 months at a temperature of less than 25° C., less than 0° C., less than −20° C., or less than −70° C.; and manufacturing a composition by incorporating the lyophilized digested tissue with a liquid.

In another aspect, a method for repairing cardiac tissue comprises injecting or implanting in a subject a composition comprising decellularized extracellular matrix derived from cardiac tissue. In some instances, said composition is injected or implanted earlier than one month following myocardial infarction. In some instances, said composition is injected or implanted earlier than two weeks following myocardial infarction. In some instances, said composition degrades within three months following injection or implantation. In some instances, said composition degrades within one month following injection or implantation. In some instances, injection or implantation of said composition repairs a congenital defect. In some instances, injection or implantation of said composition repairs damage to cardiac tissue sustained by said subject. The damage can be a myocardial infarction.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

Many features of the invention are set forth with particularity in the appended claims. A better understanding of the features and advantages of the invention will be obtained by reference to the following detailed description that sets forth illustrative embodiments, in which many principles of the invention are utilized, and the accompanying drawings of which:

DETAILED DESCRIPTION OF THE INVENTION

Figure 1:
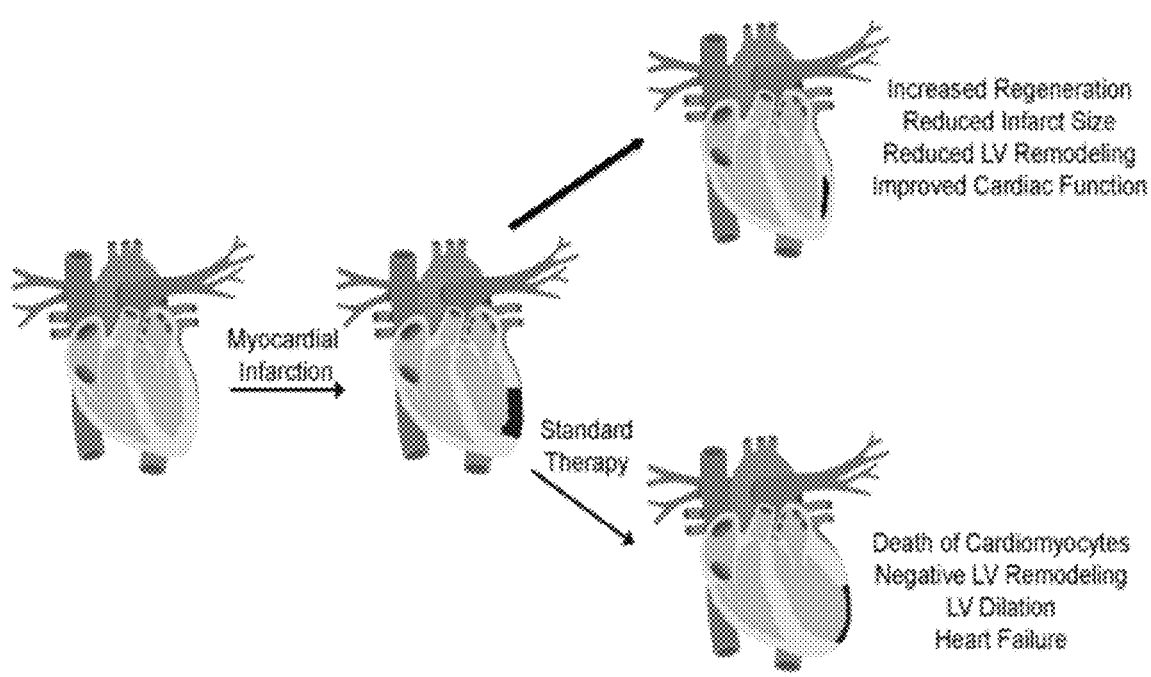
FIG. 1 illustrates an exemplary method of delivering a composition herein.

Recently investigated procedures utilize the injection of healthy cells into the left ventricle (LV) infarct wall in an attempt to regenerate and repair the myocardium, although studies have shown poor injected cell survival. Cells (including adult and embryonic stem cells, induced pluripotent stem cells, and differentiated cells such as cardiomyocytes) have been typically cultured on surfaces or scaffolds coated with one, or a few extracellular matrix (ECM) proteins. Yet, in vivo, these cells exist in a highly complex extracellular milieu; and an ECM that more closely mimics this native environment may be beneficial for cultured cell survival and function/maturation in vitro and in vivo.

Some naturally derived materials are currently being investigated for injection into the myocardium including fibrin, collagen, alginate, matrigel, and gelatin. None of these provide a significant amount of the native components of the heart extracellular matrix. For arrhythmia treatment, current non-ablative forms include injection of alginate, fibrin and cells. Existing matrices for in vitro cell culture for cardiomyocytes, stem cells, and other cardiac relevant cells include collagen, laminin, SureCoat (Cellutron, mixture of collagen and laminin), Matrigel, and gelatin.

There is a need to develop new therapies for end-stage heart failure. Currently, common treatments are heart transplantation, left ventricular (LV) assist devices, and/or current pharmaceutical regimens. These treatments do not adequately prevent post-myocardial infarction (MI) negative LV remodeling. Cellular cardiomyoplasty, or cell transplantation, has been explored for the treatment of myocardial infarction and heart failure; however, more recently acellular biomaterials have shown great promise in providing similar functional benefit without the complications associated with cell delivery. Biomaterial products for cardiac therapy have been limited because few have been manufactured specifically for the myocardium. Materials currently under investigation for injection into the myocardium include, without limitation, fibrin, collagen, alginate, matrigel, and gelatin.

In some instances, a composition as described herein comprises substantially all the constituents of cardiac ECM. In some instances, a composition comprises substantially all the constituents of cardiac ECM at similar ratios found in vivo. The ECM proteins, glycoproteins, and proteoglycans may include, without limitation: collagen types I, III, IV, V, and VI, elastin, fibrinogen, lumican, perlecan, fibulin, and/or laminin. In some instances, a composition as described herein comprises 90%, 80%, 70%, 60%, 50% or more of all the constituents of cardiac ECM at similar ratios found in vivo. In some cases, an ECM mimetic is used. For example, artificial ECM can be produced by combining either naturally-occurring or artificially-produced individual components of ECM such that the ratios of the individual components mimic the ratios found in naturally-occurring ECM.

ECM includes interstitial matrix and the basement membrane materials. In some instances, a composition comprising ECM is composed of an interlocking mesh of fibrous proteins and glycosaminoglycans (GAGs). GAGs are carbohydrate polymers and are usually attached to extracellular matrix proteins to form proteoglycans. Exemplary ECM fibers that may be included in a composition herein include, without limitation, perlecan, agrin, and collagen of all types including: fibrillar (Type I,II,III,V,XI); facit (Type IX,XII, XIV); short chain (Type VIII,X), basement membrane (Type IV), and other (Type VI,VII,XIII).

Described herein are compositions comprising heart ECM for injection into cardiac tissue. In some instances described herein, an injectable gel form of a composition derived from native heart extracellular matrix (ECM) is provided. The gel can also be used alone to recruit cells into the injured tissue or as a drug delivery vehicle. The gel can also be used to support injured tissue or change the mechanical properties. Another use of the invention is as a non-destructive conduction block to treat arrhythmias. In some instances, heart or cardiac ECM material as described herein is derived from myocardial tissue. In some instances, a composition is derived from ventricular tissue. In some instances, a composition is derived from left ventricular tissue. In some instances, a composition can be derived from left ventricular and right ventricular tissue. In some instances, a composition can be derived from autologous pericardial tissue, which may be obtained non-invasively. In other instances, heart or cardiac ECM material as described herein is derived from pericardial tissue.

The composition can be used to deliver cells into the infarct wall following a myocardial infarction.

In some instances, a composition herein mimics the extracellular matrix (ECM), for example, ECM that may have been damaged by the infarction. The composition can provide complex, myocardial specific ECM cues, which promote repair. Compositions herein are configured to be delivered via catheter technology.

Native heart ECM may have more components than traditional cell coatings and thus can demonstrate a more complex mixture of ECM components when compared to collagen and laminin. In some instances, compositions prepared as a matrix herein may mimic native heart ECM. Compositions prepared herein may increase survival or growth rate of cardiomyocytes. Compositions prepared herein may be used to plate cell cultures, such as cardiomyocyte cultures. In some instances, cultures plated on compositions herein begin beating. In some instances, cells plated on compositions herein continue beating longer than cells cultured on collagen alone. For example, cells plated on compositions herein may continue beating longer than 10, 14, 20, 25, 30, 35, 40, 45, 60, 70, 80, 90 or 100 days.

In some instances, cells growing on compositions herein have increased amounts of actinin, connexin43 or pan-cadherin. Cells growing on compositions herein may have increased survivability compared to cells growing on collagen. Also, cells growing on compositions herein may have increased attachment to the composition compared to cells growing on collagen to collagen.

In some instances, compositions provided herein comprise a variety of ECM proteins, after decellularization. The ECM proteins, glycoproteins, and proteoglycans may include, but are not limited to: collagen types I, III, IV, V, and VI, elastin, fibrinogen, lumican, perlecan, fibulin, or laminin. Thus, the decellularized myocardial ECM may comprise a complex combination of proteins and proteoglycans.

In some instances, the compositions herein are provided in an injectable form. A decellularized matrix powder may be digested to solubilize or otherwise incorporate the product in a liquid. In some instances, the incorporated product comprises glycosaminoglycans (GAG). For example, the composition may comprise a glycosaminoglycan (GAG) content of at least 1, 2, 3, 4, 5, 8, 10, 15, 20, 25, 30, 40, 50 µg per mg of lyophilized matrix or higher.

In some instances, a composition herein comprises myocardial specific ECM components. In an instance, the composition is an injectable hydrogel derived from the native myocardial ECM. In some instances, the composition does not substantially comprise any cellular antigens. In some instances, the composition does not produce an immunologic response in a subject. In some cases, the composition is delivered to the subject prior to, concurrent with or after immunosuppressive therapy. In some cases, immunosuppressive therapy is not used.

In some instances, compositions described herein are configured to be provided for therapy in an off-the-shelf manner. In an example, a composition herein is in a dry solid form and can be stored on a shelf or in a room or unit, and then solubilized with water, saline, or another liquid solution immediately before treatment.

Described herein is a composition comprising a myocardial-specific material that can be delivered via catheter to promote repair in the post-MI environment. The composition comprises a complex mixture of ventricular ECM proteins, peptides, and polysaccharides. In many instances, the composition is liquid at room temperature and forms a porous and fibrous scaffold upon injection into the myocardium. The composition promotes cell influx and preserves LV geometry and cardiac function when delivered in vivo to a myocardial infarct.

In some instances, a composition as described herein can help regenerate or repair defective or absent myocardium and restore cardiac function. Herein, an injectable extracellular matrix composition can be derived from a mammalian or synthetic source. The composition can further comprise cells. An extracellular matrix composition herein can further comprise an additional component, for example without limitation: a cell, a peptide, polypeptide, or protein, a nucleic acid such as a polynucleotide or oligonucleotide, DNA, RNA, a vector expressing a DNA of a bioactive molecule, polymer or other material, crosslinkers, and other additives like nutrients or drug molecules. One additional component can be included in the composition or several. In some cases, the additional component is a drug. In some cases, the drug is delivered as part of the extracellular matrix composition or as a component of an injected solution of ECM; in some cases the drug is delivered concurrently, before, or after the delivery of a composition described herein. Examples of drugs include, without limitation: blood pressure or hypertension medications (e.g., ACE inhibitors, alpha agonists, alpha blockers, Angiotensin II receptor blockers, diuretics, or renin blockers); antiarrhythmics (e.g., sodium channel blockers, beta blockers, potassium channel blockers, calcium channel blockers); cholesterol lowering drugs (e.g., statins, chloestyramine); blood thinners or anticoagulants (e.g., aspirin, aprotinin, clopidogrel, enoxaparin, heparin, warfarin, dabiagatran etexilate); medications that control heart rate (e.g., digitalis preparations); and/or vasodilators (e.g., nitroglycerin).

In an aspect, a composition as described herein comprises: decellularized extracellular matrix derived from cardiac tissue; and water. In some instances, the composition further comprises saline solution. A composition herein can comprise decellularized ECM derived from cardiac tissue and a liquid solution in which the decellularized ECM is miscible.

Compositions described herein can comprise a number of factors or cues in vivo, including, but not limited to: factors that promote neovascularization such as VEGF and bFGF; factors that promote cell infiltration such as SDF; factors that alter the immune response; factors that alter the inflammatory response such as IL-10; factors that promote survival of endogenous cardiomyocytes and cardiac cells; and factors that prevent apoptosis of endogenous cardiomyocytes and cardiac cells.

In some instances, methods of delivery are described wherein the composition can be placed in contact with the defective or absent myocardium, resulting in myocardial tissue regeneration and restoration of contractility, conductivity, or function to the heart muscle. In some instances, a composition herein may recruit endogenous cells and can coordinate the function of the newly recruited or added cells, allowing also for cell migration and proliferation within the composition. As described herein, in some cases, the composition can aid the repair of myocardial tissue. In some instances, such repair involves restoration of heart tissue and/or specific features of heart tissue such as striations, T-tubules, or intercalated discs.

Compositions comprising native extracellular matrix scaffolds have been prepared for use in mammals in tissue grafts procedures. Examples of the ECM matrix include without limitation: small intestine submucosa (SIS) such as the scaffolds described in U.S. Pat. No. 5,275,826, urinary bladder submucosa (UBS) such as the scaffolds described in U.S. Pat. No. 5,554,389, stomach submucosa (SS) such as the scaffolds described in U.S. Pat. No. 6,099,567, and liver submucosa (LS) or liver basement membrane (LBM) such as the scaffolds described in U.S. Pat. No. 6,379,710. In addition, collagen from mammalian sources can be retrieved from matrix containing tissues and used to form a matrix composition. Extracellular matrices can also be synthesized from cell cultures. Heart decellularization has been published for the purpose of regrowing an entire heart (Ott et al, Nature Medicine, 2008). An injectable gel form of porcine bladder matrix has also been described (Freytes et al, Biomaterials, 2008).

Disclosed herein is a biocompatible material comprising decellularized cardiac extracellular matrix derived directly from native cardiac tissue, and is used for treating defective, diseased, damaged or ischemic tissues or organs in a subject, preferably a human, by injecting or implanting the biocompatible material comprising the decellularized cardiac extracellular matrix into the subject. In some instances, the material is delivered to a non-human animal subject.

FIG. 1 illustrates an exemplary method of delivering a composition herein. FIG. 1 provides a flow of events, from myocardial infarction, to introduction of a composition described herein, resulting in such results as increased regeneration, decreased infarct size, reduced LV remodeling, and improved cardiac function.

Figure 2:
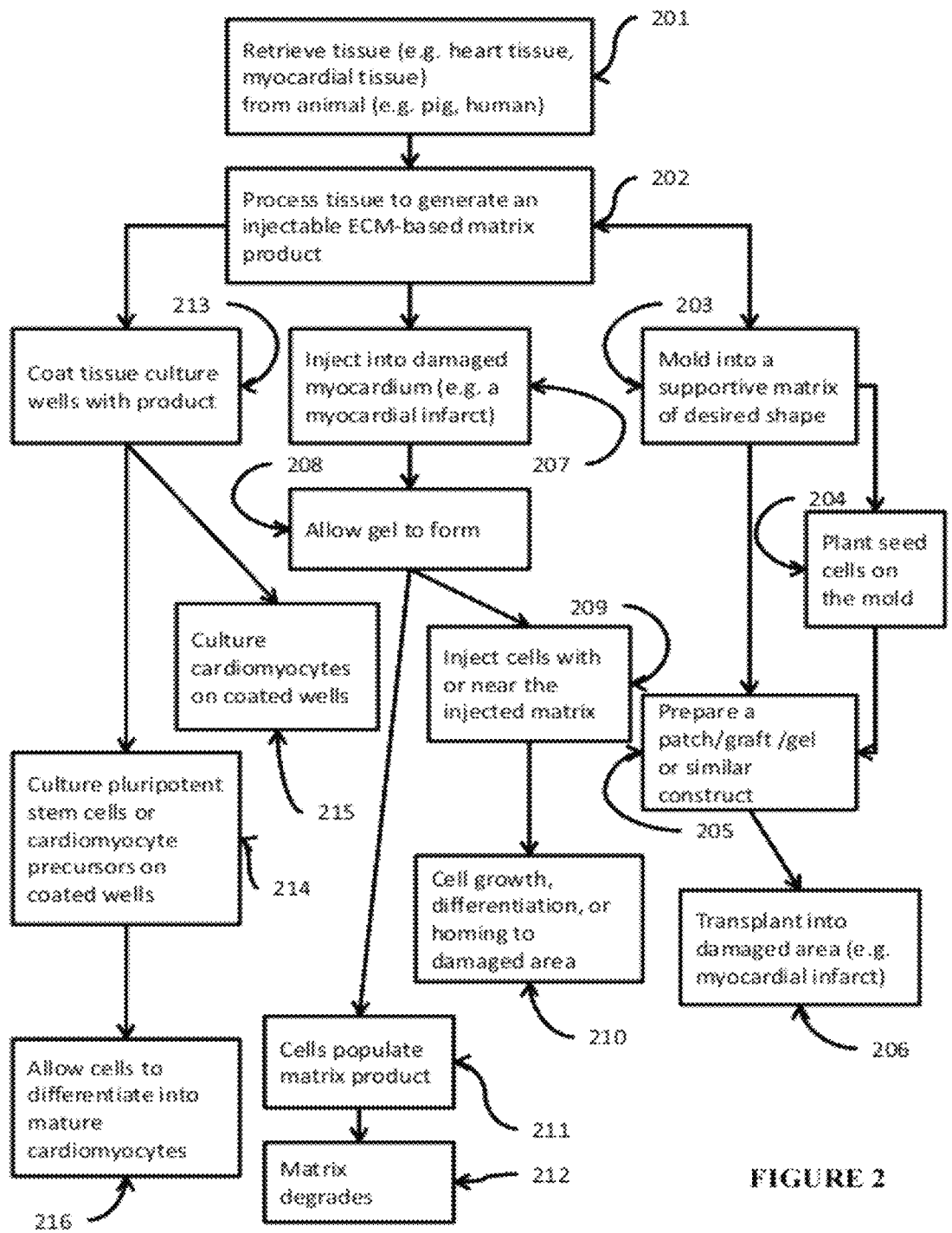
FIG. 2 illustrates various embodiments of methods and compositions described herein.

FIG. 2 is a flow diagram that illustrates several embodiments of methods and compositions provided herein. In some cases, a tissue is retrieved from an animal, 201. The tissue may be a heart tissue, e.g., myocardial tissue, but may also be other types of tissue. Various processing steps of the tissue, 202, are described herein. For example, the tissue may be decellularized, lyophilized, digested and solubilized in a desired liquid or alternatively processed through any combination of the steps described herein. As a result, an ECM-based matrix product is formed; in some embodiments, the ECM-based matrix product is injectable. In various embodiments, the ECM-based matrix product mimics the ECM of the damaged tissue in the subject, for example a myocardial ECM of a patient with a myocardial infarct.

In some embodiments, the ECM-based matrix product may be molded into a particular shape and then transplanted or introduced into a subject. The ECM-based matrix product may be molded into a supportive matrix of a desired shape, e.g., in the shape of a catheter, a stent, a graft, a patch or the like, which may be suitable for transplantation or introduction into a desired area in a subject (e.g., myocardium). Cells (e.g., seed cells) may optionally be planted or cultured on the molded ECM-based matrix product, 204. A patch, graft or gel product or a similar transplantation construct may be prepared by the method described herein, 205. The transplantation construct may be transplanted or introduced into a damaged area in a subject, 206. In some embodiments, the transplantation (or introduction) promotes cell growth or survival in the area or otherwise populates the damaged area with cells; often, the cell or tissue growth occurs directly on the ECM-based matrix.

Some embodiments relate to ECM-based matrix products that mimic ECM, e.g. myocardial ECM, 202, and methods of repairing damaged tissue or preventing damage in a tissue with the use thereof. In many cases, the ECM-based matrix product is injected, transplanted or otherwise introduced into a damaged tissue, e.g. a damaged myocardium, a myocardial infarct, 207. In some cases, a gel is allowed to form prior to or upon injection. In some embodiments, gel formation occurs after the solution enters the subject, 208. Gel formation may depend on a change of temperature, e.g., a switch to body temperature or switch to a temperature of about 37° C. Cells such as endogenous cells may then populate the ECM-based matrix product, 211. Optionally, cells are injected or otherwise introduced on or near the injection or transplantation site of the ECM-based matrix product, 209. In various embodiments, the ECM-based matrix product mimics the ECM of the damaged tissue and thus promote cell growth, differentiation or homing to the damaged area, 210. In some cases, as a result, the damaged area is populated by cells, 211 (often the cell growth occurs directly on the ECM-based matrix product). In various embodiments, the ECM-based matrix product degrades after a time sufficient to populate the damaged area with cells, 212.

This disclosure further provides compositions and methods to grow tissue cultures on tissue culture wells, 213. An ECM-based matrix product generated using the methods and compositions described herein, may be used to coat a tissue culture well. Cells of various types may be cultured on said coated culture wells. For example, cardiomyocytes may be cultured on wells coated with ECM-based matrix product, 215. In some embodiments, pluripotent stem cells, multipotent stem cells, or cardiomyocyte precursor cells are cultured on the coated wells, 214. The ECM-based matrix product may then encourage or allow cultured cells to differentiate into cells of a specific tissue, e.g. the coating may be generated using ECM-based matrix product derived from myocardial tissue and may encourage the cells to differentiate into cardiomyocytes, 216.

In still other embodiments, an ECM-based matrix product generated from artificially-created ECM may be used. In such cases, such an ECM-based matrix product may be used to coat tissue culture wells, 213, to inject into damaged myocardium (or other types of damaged tissue), 207, or molded into a supportive matrix of a desired shape, 203.

After myocardial infarction, current standard therapies such as pharmaceuticals and medical devices (or lack of therapy) are generally ineffective and eventually lead to death to the cardiomyocytes, negative LV remodeling, LV dilation, and heart failure. A method of delivering an injectable composition is described herein. In some instances, delivering a composition herein to a LV can provide increased regeneration, reduced infarct size, reduced LV remodeling, or improved cardiac function. The solution form, gel form, and adsorbed form of the heart matrix provide many of the constituents of native ECM at similar ratios found in vivo.

In some instances, the decellularized cardiac extracellular matrix is derived from native cardiac tissue selected from the group consisting of human hearts, porcine hearts, bovine hearts, or any other mammalian or animal hearts, including but not limited to, goat heart, mouse heart, rat heart, rabbit heart, and chicken heart. In some instances, the decellularized cardiac extracellular matrix is derived from native tissue from embryonic or fetal sources from tissues as described herein without additional limitations.

In yet another embodiment, the biocompatible material comprising the decellularized cardiac extracellular matrix is in an injectable gel or solution form, and can be used for cardiac repair by transplanting or delivering cells into the infarct wall following a myocardial infarction, or recruiting cells into the injured cardiac tissue. In other instances, the biocompatible material comprising a decellularized cardiac ECM is, for example, a patch, an emulsion, a viscous liquid, a gel, fragments, particles, microbeads, or nanobeads.

In another aspect disclosed herein, a composition comprises a material with a pore size of about 30 to 40 microns, wherein the material is biocompatible with cardiac tissue, and wherein the material is injectable through a catheter with an inner diameter of 25 G or smaller. In some instances, the material comprises decellularized extracellular matrix derived from cardiac tissue. In some instances, a composition comprises a material with a pore size of less than 50 microns.

In some instances, a composition herein promotes maturation of implanted cells. For example, immature cells implanted in a damaged myocardium can be implanted with or shortly following the delivery of a matrix composition as described herein, wherein the matrix composition promotes maturation of the implanted cells. In some instances, a composition promotes differentiation of implanted cells. For example, induced pluripotent stem (iPS) cells can be implanted with or shortly following the delivery of a matrix composition; and the matrix composition acts to promote differentiation of the iPS cells. In some cases, in vivo factors may also act on the iPS cells to promote differentiation, either independently or along with the matrix composition. In another example, embryonic stem (ES) cells or adult stem cells are implanted along with, or following, the delivery of a matrix composition; and the ES cells or adult stem cells are subsequently differentiated into more mature cell type. In some cases, in vivo factors may also act on the ES cells or adult stem cells to promote differentiation, either independently or along with the matrix composition.

In yet another example, a composition may promote transdifferentiation of the implanted cells. For example, non-cardiac cells may be delivered to the subject along with the composition, which promotes transdifferentiation of the cells to a cardiac phenotype. In some examples, a composition herein promotes maturation and/or promotes differentiation of the cells in vivo. In another example, a composition herein promotes maturation and/or promotes differentiation of in vitro cultured cells.

In some instances, a composition herein may further comprise growth factors that are bound to polysaccharides in a matrix material as described herein.

In some instances, biocompatible materials (e.g., materials that do not provoke an immune response in a subject) are disclosed for culturing cardiomyocytes or other cardiac relevant cells in research laboratories, or in a clinical setting prior to transplantation and for cardiac repair. Methods for manufacturing and coating a surface of tissue culture plates or wells with decellularized cardiac extracellular matrix are also provided. The biocompatible materials are also suitable for implantation into a patient.

Further provided herein is a method of producing a biocompatible material comprising the decellularized cardiac extracellular matrix of the invention. Such method comprises the steps of: (a) obtaining from a subject a cardiac tissue sample having an extracellular matrix and non-extracellular matrix components; and (b) processing cardiac tissue sample to remove the non-extracellular matrix component to obtain decellularized cardiac extracellular matrix. In certain embodiments, the cardiac tissue sample is isolated from a mammal such as a non-primate (e.g., cows, pigs, horses, cats, dogs, rats, etc.) or a primate (e.g., monkey and human), or from an avian source (e.g., chicken, duck, etc.). Decellularization procedures for the cardiac tissue sample are done using one or more physical, chemical and/or biological techniques.

For human therapy, there are many potential sources for the heart extracellular matrix material: human heart (including autologous, allogeneic, or cadaveric), porcine heart, bovine heart, goat heart, mouse heart, rat heart, rabbit heart, chicken heart, and other animal sources. In some instances, the ECM is sourced from multiple animals (e.g., multiple pigs) or multiple animal species (e.g., pigs plus a different species, such as rabbit). Unlike total heart transplantation, one donor heart could be used to treat many people. Non-human animals would be a source of heart extracellular matrix without the need for human donors. As a research reagent, non-human animal sources (porcine heart, bovine heart, goat heart, mouse heart, rat heart, rabbit heart, chicken heart, etc) can be utilized. The heart is first decellularized, leaving only the extracellular matrix and/or extracellular proteins and/or polysaccharides.

In one embodiment, the heart extracellular matrix is then lyophilized, ground up, and digested with pepsin at a low pH, or other matrix degrading enzymes such as matrix metalloproteinases. In some instances, the composition further comprises pepsin. In some instances, the composition further comprises a digestive enzyme, for example, trypsin, chymotrypsin, papain, or a combination thereof. In some instances, the composition further comprises a plurality of digestive enzymes as described herein. A digestive enzyme or enzymes for the composition here can be selected based on the peptide bonds that are cleaved by the enzyme or enzymes.

In some instances, the composition is configured to gel at body temperature (for example 37° C. or greater). In some instances, the composition is configured to gel at greater than 20, 25, 30, or 35° C. In some instances, a method of manufacturing a composition as described herein comprises selecting an enzyme based on the desired temperature of gelation of the composition. In some instances, a method of manufacturing a composition as described herein comprises selecting an enzyme based on the desired time of gelation of the composition when delivered in vivo. In some instances, the composition is in a gel form within 30, 20, 10, 5, 1 or less minutes after delivery to in vivo tissue. In some instances, one heart is decellularized in a method herein. In some instances, two or more hearts are decellularized in a method herein. In some instances, the heart tissue is obtained from multiple animals (e.g., multiple pigs) or multiple animal species (e.g., pigs plus a different species, such as rabbit). In an aspect, a method of manufacturing a composition is provided herein, the method comprising: decellularizing cardiac tissue; lyophilizing the decelled cardiac tissue; digesting the lyophilized tissue with an enzyme in a first liquid; lyophilizing the digested tissue; and manufacturing a composition by incorporating the lyophilized digested tissue with a second liquid. In some cases, incorporating in a liquid comprises solubilizing. In some cases, the method comprises many, but not all, of said steps. For example, the method may comprise decellularizing cardiac tissue, digesting the tissue with an enzyme in a first liquid, and incorporating the digested tissue with a second liquid. In some cases, the method does not comprise decellularizing cardiac tissue. In some cases, the method does not comprise incorporating digested tissue with a second liquid.

In some instances, the decellularizing is carried out by using an sodium dodecyl sulfate (SDS) solution. In some instances, the enzyme is a digestive enzyme, e.g. pepsin. In some instances, the first liquid is phosphate buffered saline (PBS), saline, or other buffered solution. In some instances, the second liquid is water, for example, sterile water, and/or deionized water, or the second liquid can be saline.

In another aspect, a composition comprises: lyophilized decellularized extracellular matrix derived from cardiac tissue. The lyophilized matrix can be miscible in water, thereby forming a solution. In some instances, the solution is a liquid solution at a temperature less than 25, 20, 15, 10, 5, or 0° C. In some instances, the solution is a gel at a temperature of more than 20, 30, 35, or 37° C. In some instances, the solution is a liquid when water is mixed with the composition and the composition is delivered in vivo.

In an instance, a composition herein demonstrates a lack of nuclei, DNA, RNA, when evaluated pathologically. In another instance, a composition herein comprises fractions of cardiac extracellular material with molecular weight bands below about 20 kDa. In some instances, a composition herein comprises glycosaminoglycan content of at least 5, 10, or 15 µg per mg of the lyophilized composition. In another instance, a composition herein comprises glycosaminoglycan content of between about 15 to 25 μg per mg of the lyophilized composition.

In some instances, a method herein further comprises lyophilizing the composition and storing the composition for up to 6 months at a temperature of less than 25° C., less than 0° C., less than −20° C., or less than −70° C.

The compositions described herein can be injected directly into a subject and thereby be used as a material therapy. For example, the solution comprising the heart extracellular matrix can be neutralized and brought up to the appropriate concentration using PBS/saline or other buffers. The solution comprising the heart extracellular matrix can then be injected through a small diameter needle into the myocardium. At body temperature, such solution then may form a gel. Cells or drugs/proteins can also be delivered inside or with the gel. For example, undifferentiated cells can be delivered inside or with the gel and such cells can be later differentiated in vivo. In other examples, partially or terminally differentiated cells are delivered inside or with the gel.

The compositions provided herein, particularly the gel reagents, can be used for tissue culture applications. The solution comprising the heart extracellular matrix may be neutralized and brought up to the appropriate concentration using PBS/saline. Such solution can then be placed into tissue culture plates/wells. Once placed in an incubator at 37° C. or above room temperature, the solution forms a gel that can be used for cell culture.

In another aspect herein, a composition is provided that comprises: decellularized extracellular matrix derived from cardiac tissue, wherein the composition is in the form of a mold. In an example, the composition is an in vitro reagent.

In an aspect, a tissue culture device comprises: a composition comprising decellularized extracellular matrix derived from cardiac tissue. In some instances, the device is a tissue culture plate. In some instances, the matrix of the device is in the shape of a mold. In some instances, the device further comprises a tissue culture medium.

In some instances, a method herein further comprises gelling the composition into a predetermined shape or mold. For example, the composition can be gelled within a tissue culture dish or plate, or the composition can be gelled to fit a certain shape of a mold. Exemplary shapes may be those of biomedical products, such as stents or catheters. Other shapes may include those configured to shape to the heart in vivo. The substrate can be cellulose. In some instances, the cellulose is in a shape for implantation into a subject. In some instances, the device further comprises a tissue culture medium. In some instances, the shape is a tissue culture shape such as, without limitation, a dish, a vial, a petri dish, a plate, a well, and a multiwall plate.

In another instance, the composition is gelled onto a shape or product to create a device coated with the composition. In another instance, the composition is gelled into a shape or mold and then lyophilized. In another instance this lyophilized shape can be implanted in vivo or used as a scaffold in vitro, or can be rehydrated prior to use In an instance, a therapeutic method for cardiac repair in a subject comprises injecting or implanting in part or in its entirety the biocompatible material of the invention. The invention further provides a therapeutic method for treating arrhythmia or other defective, diseased, damaged or ischemic tissue or organ in a subject comprising injecting or implanting the biocompatible material of the invention.

The compositions herein can comprise a decellularized ECM derived from cardiac tissue and another component or components. In some instances, the amount of ECM in the total composition is greater than 90% or 95% of the composition by weight. In some embodiments, the ECM in the total composition is greater than 1%, 5%, 10, %, 20%, 30%, 40%, 50%, 60%, 70%, or 80% of the composition by weight.

Herein, decellularized extracellular matrices are prepared such that much of the bioactivity for myocardial tissue regeneration is preserved. Exemplary bioactivity of the compositions herein include without limitation: control or initiation of cell adhesion, cell migration, cell differentiation, cell maturation, cell organization, cell proliferation, cell death (apoptosis), stimulation of angiogenesis, proteolytic activity, enzymatic activity, cell motility, protein and cell modulation, activation of transcriptional events, provision for translation events, inhibition of some bioactivities, for example inhibition of coagulation, stem cell attraction, chemotaxis, and MMP or other enzyme activity.

Herein, the compositions comprise a matrix that is substantially decellularized. In some instances, a decellularized matrix comprises no native cells. In some instances, a decellularized matrix comprises less than 1%, 2%, 3%, 4%, 5%, 6%, 7%, 8%, 9% or 10% cellular components by weight.

In some instances, a composition herein can comprise a fractionated decellularized extracellular matrix derived from cardiac tissue. For example, a composition herein comprises a matrix material with a molecular weight of less than 300 kDa, less than 200 kDa, less than 100 kDa, less than 50 kDa, or less than 20 kDa. For another example, a composition herein comprises nonaqueous matrix material with a molecular weight of less than 300 kDa, less than 200 kDa, less than 100 kDa, less than 50 kDa, or less than 20 kDa. For yet another example, a composition herein comprises matrix material with a molecular weight in a range with an upper limit of 300 kDa, 200 kDa, 100 kDa, 50 kDa, or 20 kDa and a lower limit of 0.5 kDa, 1 kDa, 2 kDa, 5 kDa, 10 kDa or 20 kDa.

In some instances, a composition herein further comprises a crosslinker, such as glutaraldehye, formaldehyde, transglutaminase, or bis-amine reactive molecules.

In some instances, a composition herein further comprises a peptide, a protein, a nucleic acid, a polynucleotide, an oligonucleotide, DNA, RNA, survival-promoting additives, proteoglycans, or glycosaminoglycans. In some instances, the composition also comprises an immunosuppressive agent. In other cases, the composition does not comprise an immunosuppressive agent.

As described herein, a composition can comprise a decellularized ECM and different tissue decellularized ECM or a synthetic or naturally occurring polymer. Exemplary polymers of a composition herein include, but are not limited to: polyethylene terephthalate fiber (Dacron), polytetrafluoroethylene (PTFE), glutaraldehyde-cross linked pericardium, polylactate (PLA), polyglycol (PGA), hyaluronic acid, polyethylene glycol (PEG), polyethelene, nitinol, and collagen from animal and non-animal sources (such as plants or synthetic collagens). In some instances, a polymer of the composition is biocompatible and biodegradable and/or bioabsorbable. Exemplary biodegradable or bioabsorbable polymers include, but are not limited to: polylactides, polyglycolides, polycarprolactone, polydioxane and their random and block copolymers. A biodegradable and/or bioabsorbable polymer can contain a monomer selected from the group consisting of a glycolide, lactide, dioxanone, caprolactone, trimethylene carbonate, ethylene glycol and lysine. The material can be a random copolymer, block copolymer or blend of monomers, homopolymers, copolymers, and/or heteropolymers that contain these monomers. The biodegradable and/or bioabsorbable polymers can contain bioabsorbable and biodegradable linear aliphatic polyesters such as polyglycolide (PGA) and its random copolymer poly (glycolide-co-lactide-) (PGA-co-PLA). Other examples of suitable biocompatible polymers are polyhydroxyalkyl methacrylates including ethylmethacrylate, and hydrogels such as polyvinylpyrrolidone and polyacrylamides. Other suitable bioabsorbable materials are biopolymers which include collagen, gelatin, alginic acid, chitin, chitosan, fibrin, hyaluronic acid, dextran, polyamino acids, polylysine and copolymers of these materials. Any combination, copolymer, polymer or blend thereof of the above examples is contemplated for use according to the invention. Such bioabsorbable materials may be prepared by known methods.

In some instances, a composition herein comprises a naturally derived polymer and ECM. Examples of naturally derived polymers for use herein include, but are not limited to: alginate, fibrin glue, and polysaccharides such as hyaluronic acid.

In an instance, a composition herein comprises a decellularized extracellular matrix derived from cardiac tissue and further comprises a biocompatible metal. An example of biocompatible metal includes, but is not limited to, titanium. In an example, a composition herein comprises small diameter fibers or small diameter particles of a biocompatible metal. The metal within the composition can provide support to the material structure. In addition, when the decellularized ECM degrades in vivo, the metal portions of the composition can be left behind in order to provide a support structure for the surrounding tissue.

In some instances, a composition herein further comprises cellulose. Cellulose can be utilized to form the material into a desired shape both in vivo and in vitro. For example, when used as a tissue culture reagent, a composition as described herein can comprise cellulose, and be set into a particular shape. In another aspect herein, a device is provided, wherein cellulose provides a substrate on which a composition as described herein is deposited. The device can then be delivered in a particular shape for tissue repair.

Commercially available ECM preparations can also be combined in the methods, devices and compositions described herein. In one embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.).

Methods are described herein of preparing an injectable composition comprising decellularized ECM derived from tissue. Related compositions, devices and methods of use also are described. The viscosity of the composition can increase when warmed above room temperature including physiological temperatures approaching about 37° C. According to one non-limiting embodiment, the ECM-derived composition is an injectable solution at room temperature and other temperatures below 35° C. In another non-limiting embodiment the gel can be injected at body temperature of 37° C. or near body temperature, but gels more rapidly at increasing temperatures. In some instances, a gel forms in less than 5 minutes at physiological temperature of 37° C. In some instances, a gel forms in less than 10 minutes at physiological temperature of 37° C. In some instances, a gel forms in less than 15 minutes at physiological temperature of 37° C. In some instances, a gel forms in less than 30 minutes at physiological temperature of 37° C. In some instances, a gel forms in less than 45 minutes at physiological temperature of 37° C. In some instances, a gel forms in less than 1 hour at physiological temperature of 37° C. In some instances, a gel forms in less than 5 minutes in vivo. In some instances, a gel forms in less than 10 minutes in vivo. In some instances, a gel forms in less than 15 minutes in vivo. In some instances, a gel forms in less than 30 minutes in vivo. In some instances, a gel forms in less than 45 minutes in vivo. In some instances, a gel forms in less than 1 hour in vivo.

In one embodiment, the heart is first decellularized, leaving only the extracellular matrix. The matrix is then lyophilized, ground or pulverized into a fine powder, and solubilized with pepsin or other enzymes. Examples of enzymes include, but are not limited to: matrix metalloproteases, collagenases, and trypsin.

In an aspect, a method of delivering a material for cardiac repair comprises: providing a lyophilized composition comprising decellularized extracellular matrix derived from cardiac tissue; sterilizing the lyophilized matrix; solubilizing the lyophilized matrix with a liquid solution, thereby forming a material; and delivering the material to cardiac tissue. In some instances the matrix is sterilized by ethylene oxide or by radiation. In some instances, the liquid solution is water, saline, or a buffer solution. In some instances, the delivery is percutaneous, for example, where the composition is delivered by a transendocardial or transcoronary a catheter. In some instances, the step of delivering the composition occurs about 1 to 30 days after a myocardial infarction. In some instances, the step of delivering the composition occurs at least 1 month or at least 1 year after a myocardial infarction. The step of delivering the composition occurs about 1 to 24 hours after a myocardial infarction. In some instances, the composition is delivered to a myocardial infarct, a border zone of a myocardial infarct, or within 2 cm or less from a myocardial infarct. For example, the step of delivering the composition can alter ventricular remodeling.

In an example for gel therapy, the solution is then neutralized and brought up to the appropriate concentration using PBS or saline. In one embodiment, the solution can then be injected through a needle into the myocardium (e.g., via catheter, through the ribs, or during an open chest procedure). The needle size can be without limitation 22 g, 23 g, 24 g, 25 g, 26 g, 27 g, 28 g, 29 g, 30 g, or smaller. In an embodiment, the needle size through which the gel is injected is 27 g. Delivery can also occur through a balloon infusion catheter or other non-needle catheter. At body temperature, the solution can then form into a gel.

In yet another aspect herein, a method for repairing cardiac tissue comprises injecting or implanting in a subject a composition comprising decellularized extracellular matrix derived from cardiac tissue. In some instances, the composition is injected or implanted earlier than one month following myocardial infarction or the composition is injected or implanted earlier than two weeks following myocardial infarction. In some instances, the composition is injected or implanted earlier than 1 day, 2 days, 3 days, 4 days, 5 days, 6 days, 1 week, 10 days, 20 days, 45 days, two months, three months, four months, 6 months or 1 year following myocardial infarction. In some instances, the composition degrades within three months or within one month following injection or implantation. In some instances, the composition degrades within 6 weeks, 2 months, 4 months, 6 months or 1 year following injection or implantation. In some instances, injection or implantation of said composition repairs a congenital defect.

In other instances, injection or implantation of said composition prevents or repairs damage to cardiac tissue sustained by said subject. The damage can be a myocardial infarct. In some instances, said repair comprises at least 20% less change in ventricular volume 3 months after said myocardial infarction as compared to a subject with cardiac tissue damage and without injection of implantation of said composition. In some instances, said repair comprises at least 5, 10, 15, 25, 30, 40, 50, 60, 70, 80 or 90% less change in ventricular volume 3 months after said myocardial infarction as compared to a subject with cardiac tissue damage and without injection of implantation of said composition. The damage can be a myocardial infarction. In some instances, said repair comprises at least 5, 10, 15, 20, 25, 30, 40, 50, 60, 70, 80 or 90% less change in ventricular volume 3 months after said injection or implantation as compared to a subject with cardiac tissue damage and without injection of implantation of said composition. In some instances, the repair comprises a 20% increase in ejection fraction 3 months after said myocardial infarct as compared to a subject with cardiac tissue damage and without injection of implantation of said composition. (An ejection fraction is a measure of cardiac function that measures the efficiency of output from the ventricles.) In some instances, the repair comprises a greater than 20, 30, 50, 75, 100 or 200% increase in ejection fraction 3 months after said myocardial infarct as compared to a subject with cardiac tissue damage and without injection of implantation of said composition.

In yet another embodiment, a gel can be injected into the infarct area, border zone, or myocardium alone or in combination with above-described components for endogenous cell ingrowth, angiogenesis, and regeneration. In yet another embodiment, a gel can also be used alone or in combination with above-described components as a matrix to change mechanical properties of the heart and/or prevent negative left ventricular remodeling. In yet another embodiment, gel can be delivered with cells alone or in combination with above-described components for regenerating myocardium. In yet another embodiment, a gel can be used alone or in combination with above-described components for creating a conduction block to treat arrhythmias.

In an exemplary method, a composition can be injected using transendocardial delivery. In this example, a NOGA guided Myostar Catheter can be used to create a three-dimensional endocardial map of electromechanical function. Using the three dimensional map, transendocardial injections of the composition can be performed at or near the site of delivery, or the site of a myocardial infarct.

In another exemplary method described herein, a composition herein can be injected using transcoronary delivery similar to intracoronary injection of bone marrow cells. In this example, an over-the-wire angioplasty balloon can be inflated at the occlusion site, and the composition can be infused via the guide wire lumen.

For soluble reagent, the solution is brought up in a low pH solution including but not limited to 0.5 M, 0.1 M, or 0.01 M acetic acid or 0.1 M HCl to the desired concentration and then placed into tissue culture plates/wells, coverslips, or other surface/3D substrate for tissue culture. After placing in an incubator at 37° C. for 1 hour, or overnight at room temperature or 4° C., the solution can be removed. After plates/wells are rinsed with PBS, cells can be cultured on the adsorbed matrix. Solution can be combined with peptides, proteins, nucleic acids, polynucleotides, oligonucleotides, DNA, RNA, drugs, nutrients, survival-promoting additives, proteoglycans, and/or glycosaminoglycans before, during, or after injection/implantation.

A reagent herein provides cell attachment and survival on both the gel and adsorbed forms of the heart extracellular matrix in vitro. The soluble reagent form of the heart extracellular matrix has been shown herein to induce faster spreading, faster maturation, and improved survival for neonatal cardiomyocytes compared to standard plate coatings.

In some instances, a composition as provided herein can comprise a matrix and comprise cells. The cells can be any variety of cells. In some instances, the cells are a variety of cardiac or cardiovascular cells including, but not limited to: stem cells, progenitors, cardiomyocytes, vascular cells, and fibroblasts derived from autologous or allogeneic sources.

A composition herein comprising ECM and cells can be prepared by culturing the cells in the ECM. In addition, where proteins such as growth factors are added into the extracellular matrix, the proteins may be added into the composition, or the protein molecules may be covalently or non-covalently linked to a molecule in the matrix. The covalent linking of protein to matrix molecules can be accomplished by standard covalent protein linking procedures known in the art. The protein may be covalently linked to one or more matrix molecules.

In an embodiment, when delivering a composition that comprises cells, the cells can be from cell sources for treating the myocardium that include autologous, non-autologous, HLA-matched, allogeneic, xenogeneic, or autogeneic sources. Accordingly, human embryonic stem cells (hESC), neonatal cardiomyocytes, myofibroblasts, mesenchymal cells, autotransplanted expanded cardiomyocytes, and adipocytes can be delivered by a composition herein. In some instances, cells herein can be cultured ex vivo and in the culture dish environment differentiate either directly to heart muscle cells, or to bone marrow cells that can become heart muscle cells. The cultured cells can then be transplanted into a mammal, either with the composition or in contact with the scaffold and other components. Myoblasts are another type of cell that lend themselves to transplantation into myocardium, however, they do not always develop into cardiomyocytes in vivo. Adult stem cells are yet another species of cell that can be part of a composition herein. Adult stem cells are thought to work by generating other stem cells (for example those appropriate to myocardium) in a new site, or they differentiate directly to a cardiomyocyte in vivo. They may also differentiate into other lineages after introduction to organs, such as the heart. In another instance, the mesenchymal stem cells are administered with activating cytokines Subpopulations of mesenchymal cells have been shown to differentiate toward myogenic cell lines when exposed to cytokines in vitro.

The following list includes some of the cells that may be used as cellular components of the composition of the invention: a human embryonic stem cell, a fetal cardiomyocyte, a myofibroblast, a mesenchymal stem cell, an autotransplanted expanded cardiomyocyte, an adipocyte, a totipotent cell, a pluripotent cell, an induced pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoietic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogeneic cell, an allogeneic cell, an adult stem cell, a post-natal stem cell, and a cardiomyocyte generated by transdifferentiation. As noted herein, differentiated cells may be used as cellular components of the compositions provided herein. Examples of differentiated cells include cardiomyocytes, cardiac myoblasts, and other cardiac cells described herein or known in the art. Such cells may be obtained by isolating the cells from an organ (e.g., heart) of an animal or person. Such cells may also be obtained by differentiating ES cells, iPS cells, adult stem cells, or other progenitor cells (for example cardiomyocyte progenitor cells). Methods of differentiation are known in the art. Such cells may also be obtained by transdifferentiation of cells of a different cell type altogether (e.g., bone marrow cells).

Human embryonic stem cell derived cardiomyocytes can be grown on a composition herein comprising a cardiac matrix. In some instances, hESC-derived cardiomyocytes grown in the presence of a composition herein provide a more in vivo-like morphology. In some instances, hESC-derived cardiomyocytes grown in the presence of a composition herein provide increased markers of maturation.

The invention is also directed to a drug delivery system comprising decellularized cardiac extracellular matrix for delivering cells, drugs, molecules, or proteins into a subject for treating defective, diseased, damaged or ischemic tissues or organs. In one embodiment, the biocompatible material comprising the decellularized cardiac extracellular matrix alone or in combination with other components is used as a non-destructive conduction block for treatment of arrhythmias. The biocompatible material can also be used to transplant cells, or injected alone to recruit native cells or act as a drug delivery vehicle. The drug delivery system herein further comprises cells, drugs, proteins, or other biological material selected from the group consisting of but not limited to erythropoietin, stem cell factor (SCF) vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (EGGS), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), matrix metalloproteinase (MMP), tissue inhibitor matrix metalloproteinase (TIMP), interferon, interleukins, cytokines, integrin, collagen, elastin, fibrillins, fibronectin, laminin, glycosaminoglycans, hemonectin, thrombospondin, heparan sulfate, dermantan, chondrotin sulfate (CS), hyaluronic acid (HA), vitronectin, proteoglycans, transferrin, cytotactin, tenascin, and lymphokines.

Tissue culture plates can be coated with either a gel form of the extracellular matrix of the invention, or an adsorbed form of the extracellular matrix of the invention to culture cardiomyocytes or other cell types relevant to cardiac repair. This can be used as a research reagent for growing these cells or as a clinical reagent for culturing the cells prior to implantation. Extracellular matrix reagent can be applied to other tissue matrices and cells.

For gel reagent, the pH of the solution can be brought toward a pH of about 6 to about 9. In some instances, the pH is brought to a physiological pH of about 7.4. The gel is then brought up to the appropriate concentration using PBS/saline or other buffer, and then placed into tissue culture plates and/or wells. Once placed in an incubator at 37° C., the solution can form a gel that can be used for any 2D or 3D culture substrate for cell culture. In one embodiment, gel can be crosslinked with glutaraldehye, formaldehyde, bis-NHS molecules, or other crosslinkers, or be combined with cells, peptides, proteins, DNA, drugs, nutrients, survival promoting additives, proteoglycans, and/or glycosaminoglycans, or combined and/or crosslinked with a synthetic polymer for further use.

The invention further provides a method of culturing cells on an adsorbed matrix comprising the steps of: (a) providing a solution comprising the biocompatible material of the invention in a low pH solution including but not limited to 0.5 M, or 0.01 M acetic acid or 0.1 M HCl to a desired concentration, (b) placing said solution into tissue culture plates or wells, (c) incubating said tissue culture plates or wells such as at 37° C. for 1 hour, or overnight at room temperature or 4° C., (d) removing said solution, (e) rinsing said tissue culture plates or wells with PBS, and (f) culturing cells on the adsorbed matrix. Cells that can be cultured on the adsorbed matrix comprising the heart extracellular matrix of the invention are cardiomyocytes or other cell types relevant to cardiac repair.

In some instance a composition comprises crosslinkers including, but not limited to: common collagen crosslinkers, HA crosslinkers, or other protein cross-linkers with altered degradation and mechanical properties.

In an instance, a method of making the composition herein comprises electrospinning. In some instances, a method herein is configured to control the nanofiber size, shape, or thickness.

In some instances, a composition herein may contain microbeads. Microbeads can be a part of the composition or delivered by the composition. Exemplary microbeads can be any variety of materials, for example, natural or synthetic. In some instances, the microbeads can have varied degradation properties or comprise, for example, MMP inhibitors, growth factors, or small molecules.

In some instances, the composition can comprise a biological group that can act as an adhesive or anchor where the composition is delivered.

In an instance, a composition here can be a bioadhesive, for example, for wound repair. In some instances, a composition herein can be configured as a cell adherent. For example, the composition herein can be coating or mixed with on a medical device or a biologic that does or does not comprises cells. For example, the composition herein can be a coating for a synthetic polymer vascular graft. In some instances, the composition is anti-bacterial or anti-bacterial agents could be included.

Methods herein can comprise delivering the composition as a wound repair device. For example, after cardiac ablation, the composition can be delivered to improve healing.

In an instance, a composition here comprises an alginate bead that is coated with an ECM composition as described herein.

In some instances, a composition is injectable. An injectable composition can be, without limitation, a powder, liquid, particles, fragments, gel, or emulsion. The injectable composition can be injected into a heart or in many instances, injected into the left ventricle, right ventricle, left atria, right atria, or valves of a heart. The compositions herein can recruit, for example without limitation, endothelial, smooth muscle, cardiac progenitors, myofibroblasts, stem cells, and cardiomyocytes.

Methods of making the compositions herein can include decellularizing tissue from any age animal or human.

Methods herein include delivery of a composition comprising an ECM. Exemplary methods include, but are not limited to: direct injection during surgery; direct injection through chest wall; delivery through catheter into the myocardium through the endocardium; delivery through coronary vessels; and delivery through infusion balloon catheter.

In some instances, a composition herein is a coating. A coating can be used for tissue culture applications, for both research and clinical. The coating can be used to coat, for example without limitation, synthetic or other biologic scaffolds/materials, or implants. In some instances, a coating is texturized or patterned. In some instances, a method of making a coating includes adsorption or chemical linking. A thin gel or adsorbed coating can be formed using a solution form of the composition.

The disclosure is further illustrated by the following examples, which are not to be construed in any way as imposing limitations upon the scope thereof. It is apparent for skilled artisans that various modifications and changes are possible and are contemplated within the scope of the current invention.

EXAMPLE 1

The objective of this study is to examine the use of a gel as a growth platform for cell adhesion, growth, maturation, and delivery in vivo. It is provided that a gel composed of native heart extracellular matrix tissue can aid in cardiac tissue regeneration by promoting cell survival.

Female Sprague Dawley rats were euthanized and their hearts decellularized. Decellularized hearts were then lyophilized, rehydrated, pulverized, and lyophilized again to form a dry powder. Frozen hearts were rehydrated with water and then immersed in liquid nitrogen. Once frozen, hearts were systematically crushed within a ball and cup apparatus at 70 psi for 10 seconds. Pulverized heart particulates were then freeze dried. Once dry, lyophilized heart tissue was combined with 1% pepsin and amalgamated with 0.01M HCl to a concentration of 10 mg/mL. Solution was stirred at room temperature for 48 hours to allow for solubilization of the extracellular matrix tissue. After 48 hours, the HCl solution was aliquoted into Eppendorf tubes on ice and neutralized with 0.1N NaOH to pH 7.4.

Through the methods described above, a native rat cardiac ECM gel has been formed. Successful gelation of 2.5-8 mg/mL gels occurred within 15 min, as confirmed by the increased viscous nature of the material. Increased stiffness was observed with higher density gels. The pH-adjusted solution was diluted to concentration with 1×PBS, plated on a 96 well plate at 50 μL per well, and then transferred to an incubator at 37° C. and 5% CO2. After the gel had formed, 100 μL of isolated 2d neonatal cardiomyocyte cells were pipetted on top of the gel at 60,000 cells per well. After a few days, cells were examined for adherence to the gels.

Plating cardiomyocytes on the cardiac ECM gels at $1 \times 10^4$ showed successful adhesion and survival of cells to the ECM. The cells were cultured on the ECM for up to four days.

One hundred mL of cardiac ECM solution (7 mg/mL) was injected through a 30 G needle into the LV free wall of an anesthetized rat. In summary, the study shows that native heart extracellular matrix can be isolated, solubilized, and self-assembled into a gel when brought to physiological pH and temperature.

EXAMPLE 2

Here, cell coating use has been investigated for native heart extracellular matrix of adult ventricles that have been decellularized and solubilized. The advantages being that native heart ECM may have more components than traditional cell coatings, and be more readily available for use than pretreatment with other cell types.

Hearts were removed from Sprague-Dawley rats, and decellularized. The decellularized hearts were lyophilized, rehydrated, and pulverized after freezing in liquid nitrogen. The ECM was then digested in pepsin in 0.1M HCl. After 48 hours of digestion, 0.01 M acetic acid was added to dilute to the final concentration of 1 mg/ml.

Pepsin digestion of the native heart ECM was run in vertical gel electrophoresis in reducing conditions using dithiothreirol (DTT) and compared against laminin (BD Biosciences), and calf skin collagen (Sigma). Gels were stained with Imperial Protein Stain (Pierce). Native heart ECM can demonstrate a more complex mixture of ECM components when compared to collagen and laminin.

Cardiac myocytes were harvested from the ventricles of 1 to 2 day old Sprague-Dawley rats using an isolation kit (Cellutron, Highland Park, N.J.). The initial supernatant was discarded, but the subsequent 20 min digestions were strained and suspended in DMEM supplemented with 17% M199, 10% horse serum, 5% fetal bovine serum, and 1% penicillin/streptomycin. After isolation, the supernatant was pre-plated onto tissue culture polystyrene dishes to increase purity of cardiomyocytes through selective adhesion of fibroblasts.

Either 1 mg/ml native cardiac ECM or Collagen I (Sigma, St. Louis, Mo.) was adsorbed onto tissue culture 48-well plates for 1 hour at 37° C. Isolated neonatal cardiomyocytes were plated at a density of 200,000/cm2 and media was changed to low serum maintenance media after 24 hours (DMEM, 18.5% M199, 5% HS, 1% FBS and 1% penicillin/streptomycin). Cell cultures were maintained at 37° C. and 5% carbon dioxide, monitored daily, and fresh media was added every 2-3 days. Cultures were fixed at day 2, day 4, and day 7 and stained for alpha actinin, connexin43, pan-cadherin, actin and nuclei. Cardiomyocytes began to spontaneously beat in culture at Day 2. Cells cultured on collagen began detaching from the plate at Day 8. One set of cells cultured on native heart ECM continued beating until Day 45. All cells cultured on collagen stopped beating at Day 14.

The native cardiac ECM was shown by this study to contain more complex components when compared to other standard cell culture coatings. Neonatal rat cardiomyocytes attached to native heart ECM as a coating for cell culture, spontaneously began beating. Cardiomyocytes cultured on native cardiac ECM demonstrated increased actinin, connexin43, and pan-cadherin staining over time. Also, the neonatal cardiomyocytes had increased survivability and attachment on the native heart ECM when compared to collagen.

EXAMPLE 3

Myocardial infarction was induced in rats using a 25 min ischemia-reperfusion model, via occlusion of the left anterior descending artery. At one week post-MI baseline function was calculated from MRI images. Porcine myocardial ECM was decellularized in small pieces, in 1% SDS for several days, followed by a DI rinse overnight, lyophilization and milling to create a powder. Digestion was performed in 0.1 M HCl with pepsin to create a solubilized form of the material.

Solubilized ECM was brought to pH 7.4 using 1 M NaOH and diluted with PBS to be 6 mg/mL prior to injection. After MI surgery, animals were randomized into two groups and ECM or saline was injected into the LV free wall of female Sprague Dawley rats through a 30 G needle, two weeks after infarction surgery.

4 weeks after injection surgery (6 weeks post-MI), cardiac function was again assessed using MRI.

Animals injected with ECM showed preserved function (as evaluated based on ejection fraction) at 6 weeks, while saline injected animals did not maintain cardiac function. End diastolic and end systolic volume were also preserved in ECM injected animals.

EXAMPLE 4

Currently, stem cells and other cell types are in clinical trials for treatment of heart failure by delivery through a 27 G catheter into the myocardial wall. Porcine ventricular tissue was decellularized using SDS detergents, and processed to form a solubilized form of the matrix, and neutralized to physiologic pH and diluted to 6 mg/mL for injection.

Two Yorkshire pigs received a coil-induced myocardial infarction and were injected with myocardial matrix alone or with cells at two months post infarction.

Derived from fetal cardiac explants were pre-labeled with a fluorescent dye, 1,1'-Dioctadecyl-3,3,3',3'-tetramethylindocarbocyanine (DiI), which is a cytoplasmic stain, for histological identification. A pro-survival cocktail, shown to enhance hESC survival in a rodent model, was used.

Matrix alone or with cells was injected at a clinically relevant rate of 0.2 mL per 30 seconds through a catheter, as guided by NOGA mapping. 5 injections of 0.1 mL each were made of matrix alone or with cells into border zone regions of the infarct.

Matrix alone and matrix with cells were able to be successfully injected into the porcine heart, minimally invasively, without clogging the narrow catheter.

EXAMPLE 5

Porcine ventricular myocardium is decellularized, and cell removal is confirmed by hematoxylin and eosin (H&E) staining of fresh frozen decellularized tissue sections. Following this decellularization procedure, the ECM is lyophilized and then milled into a fine particulate. The myocardial ECM powder was characterized using Liquid Chromatography Mass Spectrometry (LC-MS/MS), which allows for the identification of proteins and proteoglycans. LC-MS/MS revealed a variety of ECM proteins, indicating retained protein content after decellularization. The ECM proteins, glycoproteins, and proteoglycans identified include: collagen types I, III, IV, V, and VI, elastin, fibrinogen, lumican, perlecan, fibulin, and laminin. The identification of these components within the decellularized myocardial ECM indicates a retained complex combination of proteins and proteoglycans.

To generate the injectable form of the composition, decellularized matrix powder is solubilized through enzymatic digestion. The matrix is allowed to digest for 48 hr under constant stirring. It was determined that the glycosaminoglycan (GAG) content of the solubilized product was 23.2±4.63 μg per mg of matrix.

EXAMPLE 6

The liquid composition is brought up to physiologic pH through the addition of NaOH and 10×PBS, and diluted to its final concentration with 1×PBS. At this point, the product can be used immediately, or can be lyophilized, stored frozen, and rehydrated with sterile water prior to use.

The composition self-assembles into a hydrogel upon transendocardial injection in vivo into 25 injection sites (0.2 mL each site) throughout the septal wall and LV free wall. Detection of the matrix within the LV free wall and septal wall confirmed successful delivery into the myocardium, as well as gelation of the matrix in vivo. No material was observed in satellite organs.

EXAMPLE 7

Figure 3:
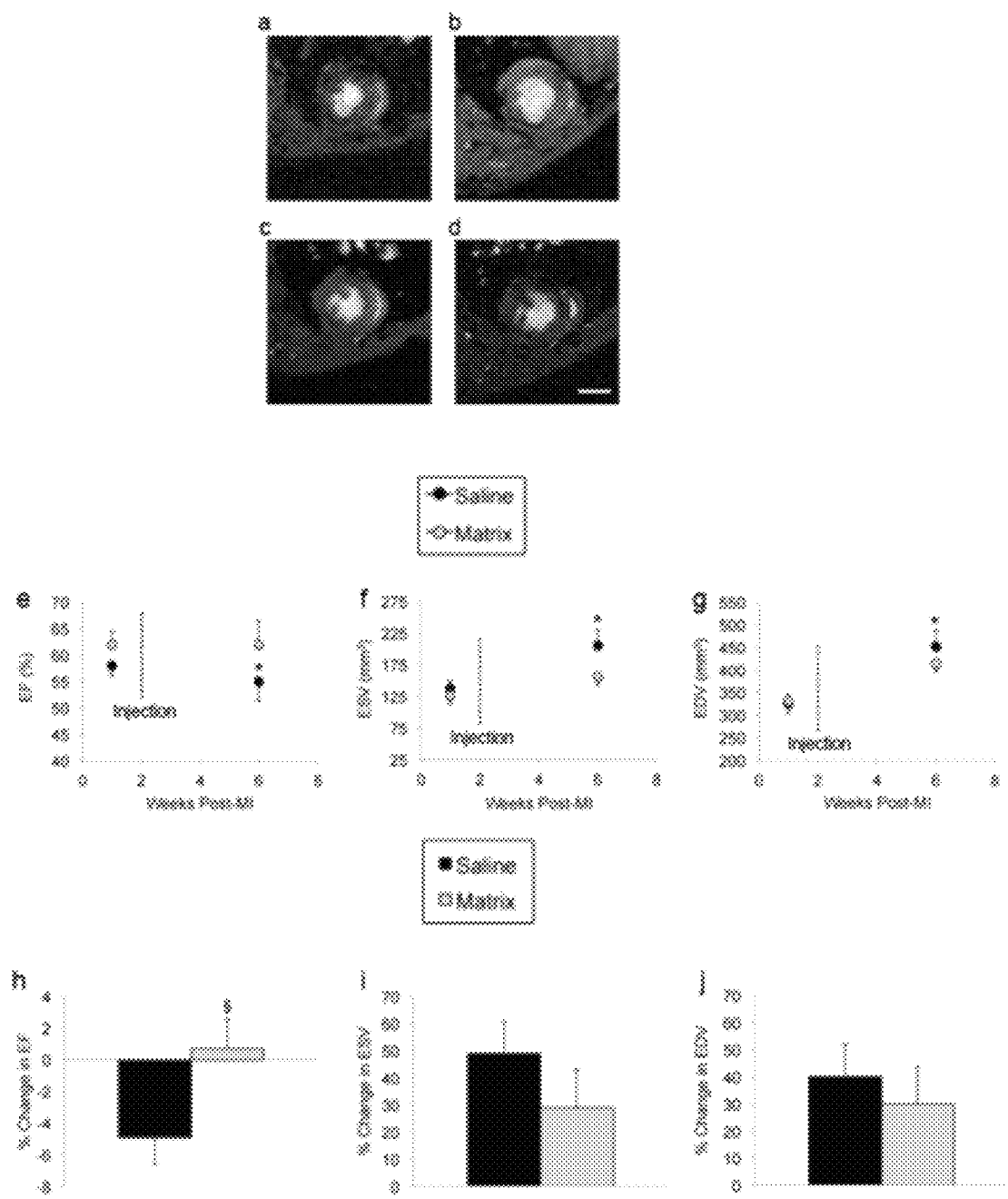
FIG. 3 demonstrates data from the injection of a composition herein into a rat heart.

A composition prepared according to Examples 5 and 6 (referred to in this example as "Composition") was used in the present example. Composition (n=6) or saline (n=6) was injected into the LV free wall of female Sprague Dawley rats two weeks after infarction. Magnetic resonance imaging (MRI) was used to assess cardiac function and LV geometry one week post-MI, as a pre-treatment baseline, and at six weeks post-MI. Both the LV volume and ejection fraction at four weeks post-injection remained statistically equivalent to baseline measurements in composition injected animals, whereas both worsened in the saline control animals as demonstrated in Table 1. The LV volume and ejection fraction at four weeks post-injection remained statistically equivalent to baseline measurements in injected animals, whereas both worsened in the saline control animals (FIG. 3). FIG. 3 demonstrates pre- and post-injection of saline (a, b) and Composition (c,d) (*$P<0.05$ compared to baseline; §$P=0.054$). There were also trends in improvement in the percent changed in EF and volumes.

TABLE 1

| MRI data | | |
|---|---|---|
| | 1 week post-MI (1 week pre-injection) | 4 weeks post-injection |
| Ejection Fraction | | |
| Saline | 58 ± 6% | 55 ± 11%* |
| Composition | 62 ± 5% | 62 ± 9% |
| End Diastolic Volume (mm$^3$) | | |
| Saline | 325 ± 49 | 451 ± 90* |
| Composition | 331 ± 66 | 414 ± 45 |
| End Systolic Volume (mm$^3$) | | |
| Saline | 137 ± 32 | 205 ± 61* |
| Composition | 126 ± 34 | 157 ± 37 |

EXAMPLE 8

Figure 4:
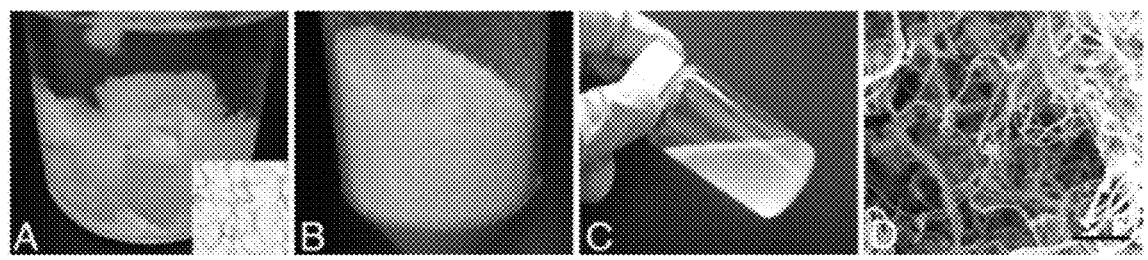
FIG. 4 illustrates some exemplary steps of a method of manufacturing a composition as described herein.

Porcine ventricular myocardium is decellularized (FIG. 4A), and cell removal is confirmed by hematoxylin and eosin (H&E) staining of fresh frozen decellularized tissue sections, staining with Hoechst 33342, and through a DNEasy kit. Following this decellularization procedure, the ECM is lyophilized and then milled into a fine particulate (FIG. 4B). The myocardial ECM powder was characterized using Liquid Chromatography Mass Spectrometry (LC-MS/MS), which allows for the identification of proteins and proteoglycans. LC-MS/MS revealed a variety of ECM proteins, indicating retained protein content after decellularization. The ECM proteins, glycoproteins, and proteoglycans identified include, without limitation: collagen types I, III, IV, V, and VI, elastin, fibrinogen, lumican, perlecan, fibulin, and laminin. The identification of these components indicates a retained complex combination of proteins and proteoglycans.

To generate the injectable form, decellularized matrix powder is processed into a liquid through enzymatic digestion. The matrix is allowed to digest for 48 hr under constant stirring, yielding liquid. Complete digestion is confirmed by lack of visible particles in solution (FIG. 4C), as well as the presence of low molecular weight species with gel electrophoresis. In some instances, a composition herein lacks nuclei/DNA, has molecular weight bands below 20 kDa, has a GAG content between 15-25 µg/mg of matrix, and lack of visible particles after 48 hr of digestion. Liquid is brought up to physiologic pH through the addition of NaOH and 10×PBS, and diluted to its final concentration (6 mg/mL, which has already been optimized for appropriate gelation characteristics) with 1×PBS. At this point, the product can be used immediately, or can be lyophilized, stored frozen, and rehydrated with sterile water prior to use. To induce gelation in vitro, the solution is brought up to 37° C., which forms a porous and fibrous scaffold similar in scale and structure as native ECM (FIG. 4D). Or the material can also be injected in vivo where it self-assembles into a hydrogel. While preferred embodiments of the invention have been shown and described herein, it will be obvious to those skilled in the art that such embodiments are provided by way of example only.

Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising digested, decellularized extracellular matrix derived from cardiac tissue, the extracellular matrix having a pore size of about 30 to 40 microns, wherein the composition is injectable through a catheter with an inner diameter of 25G or smaller, and wherein the extracellular matrix comprises glycosaminoglycan in a concentration of between about 60 to 120 µg mL of the extracellular matrix.

2. The composition of claim 1, wherein the composition further comprises at least one digestive enzyme.

3. The composition of claim 2, wherein the at least one digestive enzyme cleaves the matrix such that the composition gels at greater than 20° C. or wherein the at least one digestive enzyme cleaves the matrix such that the composition gels in less than 30 minutes.

4. The composition of claim 1, wherein the digested, decellularized extracellular matrix is derived from ventricular tissue.

5. The composition of claim 1, wherein the composition further comprises a growth factor.

6. The composition of claim 1, wherein the composition is in a gel form within 30 minutes after delivery to in vivo tissue.

7. The composition of claim 1, wherein the composition comprises factors that promote survival of endogenous cardiomyocytes and cardiac cells.

8. The composition of claim 1, wherein the composition comprises: alginate and water.

9. A tissue culture device comprising: a composition comprising digested, decellularized extracellular matrix derived from cardiac tissue, the extracellular matrix having a pore size of about 30 to 40 microns; and a substrate, wherein the tissue culture device is used for in vitro tissue culture; and wherein the extracellular matrix comprises from about 10 to about 20 ug of glycosaminoglycans per mg of the extracellular matrix.

10. The device of claim 9, wherein the substrate is a tissue culture plate.

11. The device of claim 9, wherein the matrix is in the shape of a mold.

12. The device of claim 9, wherein the matrix is molded to the shape of the substrate.

13. A method for repairing cardiac tissue comprising injecting in a subject the composition of claim 1.

14. The method of claim 13, wherein said composition is injected earlier than one month following myocardial infarction.

15. The method of claim 13, wherein said composition degrades within three months following injection or implantation.

16. The composition of claim 1, wherein following injection or implantation in a subject, the composition degrades within three months.

17. The composition of claim 1, wherein the material transitions to gel from in vivo.

18. The composition of claim 1, wherein the digested, decellularized extracellular matrix derived from cardiac tissue is enzymatically digested.

* * * * *